United States Patent
Shen et al.

(10) Patent No.: US 11,154,637 B2
(45) Date of Patent: Oct. 26, 2021

(54) BIODEGRADABLE SEALANT AND USE OF A BIODEGRADABLE SEALANT IN MANUFACTURE OF AN AGENT FOR BIOLOGICAL TISSUE ADHESION OR REPAIR

(71) Applicant: INDUSTRIAL TECHNOLOGY RESEARCH INSTITUTE, Hsinchu (TW)

(72) Inventors: Hsin-Hsin Shen, Zhudong Township (TW); Yu-Chi Wang, New Taipei (TW); Sen-Lu Chen, Zhunan Township (TW); Yu-Bing Liou, Hsinchu (TW); Jian-Wei Lin, Tainan (TW); Yi-Hsuan Lee, Taipei (TW); Ming-Chia Yang, Taipei (TW); Ying-Wen Shen, Zhunan Township (TW); Wei-Lin Yu, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/675,860

(22) Filed: Nov. 6, 2019

(65) Prior Publication Data
US 2020/0197563 A1 Jun. 25, 2020

Related U.S. Application Data

(63) Continuation-in-part of application No. 16/287,663, filed on Feb. 27, 2019, now abandoned.
(Continued)

(30) Foreign Application Priority Data
Nov. 4, 2019 (TW) .................................. 108139907

(51) Int. Cl.
*A61L 24/06* (2006.01)
*A61L 24/00* (2006.01)

(52) U.S. Cl.
CPC ........... *A61L 24/06* (2013.01); *A61L 24/0042* (2013.01)

(58) Field of Classification Search
CPC ....... A61L 24/06; A61L 24/0042; C08L 71/02
See application file for complete search history.

(56) References Cited

U.S. PATENT DOCUMENTS 5,962,420 A 10/1999 Edwardson et al.
7,999,023 B2 8/2011 Menon et al.
(Continued)

FOREIGN PATENT DOCUMENTS

CN 106009241 A 10/2016
CN 107320766 A 11/2017
(Continued)

OTHER PUBLICATIONS

Singer et al. (American Journal of Emergency Medicine 2008;26:490-496) (Year: 2008).*
(Continued)

*Primary Examiner* — Ernst V Arnold
(74) *Attorney, Agent, or Firm* — Birch, Stewart, Kolasch & Birch, LLP

(57) ABSTRACT

A biodegradable sealant includes: a polyethylene glycol derivative; a photoinitiator; and a solvent, wherein the content of the polyethylene glycol derivative is about 10-75 wt % in the biodegradable sealant. The polyethylene glycol derivative is obtained by a substitution reaction, and in the substitution reaction, the polyethylene glycol is modified with methacrylic anhydride.

25 Claims, 18 Drawing Sheets
(7 of 18 Drawing Sheet(s) Filed in Color)

Related U.S. Application Data

(60) Provisional application No. 62/756,740, filed on Nov. 7, 2018.

(56) References Cited

U.S. PATENT DOCUMENTS

| | | |
|---|---|---|
| 8,263,720 B1 | 9/2012 | Salamone et al. |
| 8,946,305 B2 | 2/2015 | Liao et al. |
| 2010/0112036 A1 | 5/2010 | Zhang et al. |
| 2011/0002997 A1* | 1/2011 | Elisseeff ............... A61K 8/8152 424/486 |
| 2015/0090482 A1* | 4/2015 | Shimura ............... C08F 220/20 174/258 |
| 2015/0182657 A1 | 7/2015 | Rieske et al. |

FOREIGN PATENT DOCUMENTS

| | | |
|---|---|---|
| JP | 2014-177460 A | 9/2014 |
| TW | 200940597 A | 10/2009 |
| TW | I486381 B | 6/2015 |

OTHER PUBLICATIONS

Bryant et al. (J Biomed Mater Res. 2002;59:63-72) (Year: 2002).*
Lin-Gibson et al. (Biomacromolecules 2004;5:1280-1287) (Year: 2004).*
Sigma Aldrich ([online] retrieved on Dec. 11, 2020 from: https://www.sigmaaldrich.com/catalog/product/aldrich/410896?lang=en&region=US&cm_sp=Insite-_-caSrpResults_srpRecs_srpModel_irgacure%20d-2959-_-srpRecs3-1 ; 2020; 4 pages). (Year: 2020).*
Patel et al. (Adv Healthcare Mater. 2017,6:7 pages). (Year: 2017).*
Zhang et al. [online], https://tsapps.nist.gov/publication/get_pdf.cfm?pub_id=852330 (Accessed Jul. 26, 2021)American Chemical Society Division of Polymer Chemistry|228th | |ACS; 2004; 2 pages. (Year: 2004).*
Annabi et al., "Surgical Materials: Current Challenges and Nano-enabled Solutions", Nano Today, vol. 9, No. 5, Oct. 1, 2014, pp. 574-589.
Behrens et al., "Biodegradable Polymer Blend Based Surgical Sealant with Body Temperature Mediated Adhesion", Advanced Materials, vol. 27, No. 48, Dec. 22, 2015, pp. 8056-8061.
Chen et al., "A PEG-Based Hydrogel for Effective Wound Care Management", Cell Transplantation, vol. 27, No. 2, 2018, pp. 275-284.
Kim et al., "Polyethylene Glycol Hydrogel Spinal Sealant (DuraSeal Spinal Sealant) as an Adjunct to Sutured Dural Repair in the Spine", SPINE, vol. 36, No. 23, 2011, pp. 1906-1912.
Lang et al., "A Blood-Resistant Surgical Glue for Minimally Invasive Repair of Vessels and Heart Defects", Science Translational Medicine, vol. 6, Issue 218, Jan. 8, 2014, pp. 1-10.
Liu et al., "In vivo study of novelly formulated porcine-derived fibrinogen as an efficient sealant", Journal of Materials Science, vol. 26, No. 146, 2615, pp. 1-7.
Patenaude et al., "Injectable, Mixed Natural-Synthetic Polymer Hydrogels with Modular Properties", Biomacromolecules, vol. 13, 2012. pp. 369-378.
Reid et al., "PEG Hydrogel Degradation and the Role of the Surrounding Tissue Environment", Journal of Tissue Engineering and Regenerative Medicine, vol. 9, No. 3, Mar. 2015, 6 pages.
Scognamiglio et al., "Adhesive and sealant interfaces for general surgery applications", Journal of Biomedical Materials Research B: Applied Biomaterials, vol. 104B, Issue 3, Apr. 2016, pp. 626-639.
Van Hove al., "Microwave-assisted Functionalization of Poly(ethylene glycol) and On-resin Peptides for Use in Chain Polymerizations and Hydrogel Formation", Journal of Visualized Experiments, vol. 80, Oct. 2013, pp. 1-15.
Taiwanese Office Action for Appl. No. 108139907 dated Sep. 9, 2020.

* cited by examiner (A)
The sealant of the present disclosure (B)
The sealant of the present disclosure (C)

ColoSkin H&E stain 40X

The sealant of the present disclosure
H&E stain 40X

ColoSkin
Masson's trichrome stain 40X

The sealant of the present disclosure Masson's trichrome stain 40X

BIODEGRADABLE SEALANT AND USE OF A BIODEGRADABLE SEALANT IN MANUFACTURE OF AN AGENT FOR BIOLOGICAL TISSUE ADHESION OR REPAIR

CROSS REFERENCE TO RELATED APPLICATIONS

This application is a Continuation-In-Part of application Ser. No. 16/287,663, filed on Feb. 27, 2019, which claims the benefit of provisional Application No. 62/756,740, filed on Nov. 7, 2018, the entirety of which is incorporated by reference herein.

The present application is based on, and claims priority from, Taiwan Application Serial Number 108139907, filed on Nov. 4, 2019, the disclosure of which is hereby incorporated by reference herein in its entirety.

TECHNICAL FIELD

The present disclosure relates to a sealant, and in particular it relates to a biodegradable sealant and the use of a biodegradable sealant in the manufacture of an agent for bond or repair of biological tissue.

BACKGROUND

Techniques such as suturing, stapling, and the like are commonly available today for reattachment and suturing tissue during surgery. These techniques still have some limitations in clinical use for minimally invasive surgery, however. For example, the use of surgical sutures for wound closure takes time and may cause injury or infection to the surrounding tissue, and it cannot immediately prevent leakage of body fluids from the wound and block air from coming into contact with the wound.

The application of adhesives may provide a convenient alternative for wound closure. It provides advantages, such as a simple implant procedure, a shorter healing time, less patient suffering, and there is no need for a secondary surgical removal.

However, it is still challenging to achieve an adhesive with strong adhesion strength in a soft tissue, and it is necessary to simultaneously reduce the toxicity of the material, the damage to the surrounding tissue, and the side effects caused by the sealing material.

Another limitation of adhesives is that most commercially available adhesives provide very low bonding strength in humid environments, which are filled with body fluids and highly kinetic areas of the body. Most clinically available glues or sealants provide no elasticity and no good adhesion.

Therefore, there is a need for a novel sealant that is biodegradable, non-cytotoxic, and effective in binding biological tissue in a humid environment.

SUMMARY

The present disclosure provides a biodegradable sealant comprising: a polyethylene glycol derivative; a photoinitiator; and a solvent, wherein the content of the polyethylene glycol derivative in the biodegradable sealant is about 10-75 wt %. The polyethylene glycol derivative is obtained through a substitution reaction, and in the substitution reaction, the polyethylene glycol is modified with methacrylic anhydride The present disclosure also provides a use of a biodegradable sealant in the manufacture of an agent for bond or repair of biological tissue, wherein the biodegradable sealant is the biodegradable sealant mentioned above.

A detailed description is given in the following embodiments with reference to the accompanying drawings.

BRIEF DESCRIPTION OF DRAWINGS

The patent or application file contains at least one color drawing. Copies of this patent or patent application publication with color drawing will be provided by the USPTO upon request and payment of the necessary fee.

The present invention can be more fully understood by reading the subsequent detailed description and examples with references made to the accompanying drawings, wherein.

DETAILED DESCRIPTION

Figure 1:
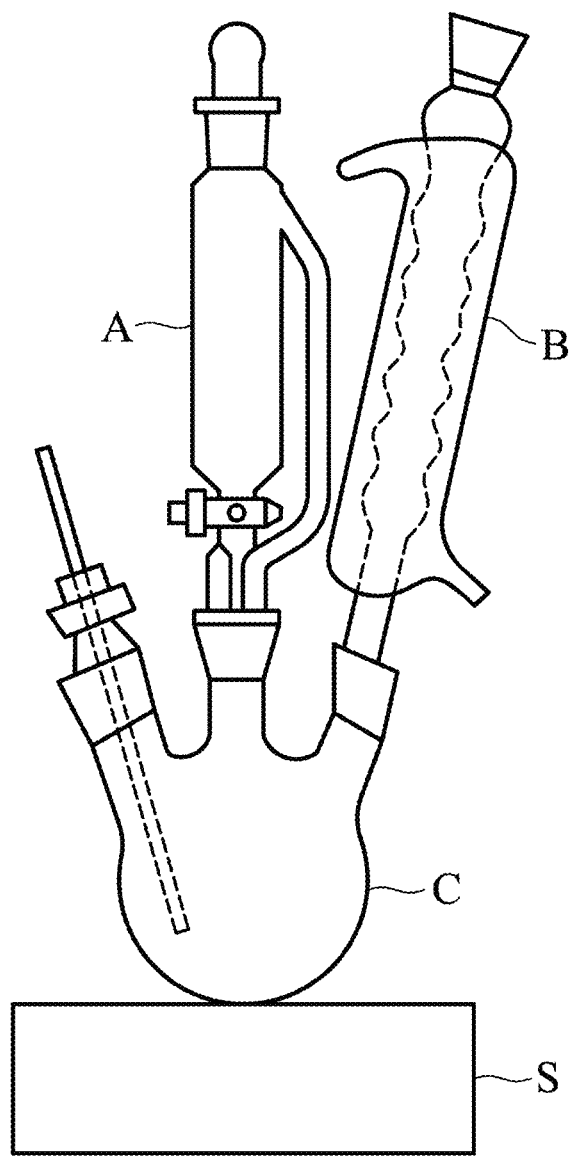
FIG. 1 shows a refluxing and dropping reaction device 100 used in the synthesis of the polyethylene glycol derivative of the present disclosure in one embodiment.

In the following detailed description, for purposes of explanation, numerous specific details are set forth in order to provide a thorough understanding of the disclosed embodiments. It will be apparent, however, that one or more embodiments may be practiced without these specific details.

The present disclosure provides a biodegradable sealant which can be applied to bond or repair of biological tissue.

The biodegradable sealant of the present disclosure mentioned above is a viscous liquid, and thus can be easily applied to the biological tissue to be bonded or repaired, and can be cured in a short time by illumination to effectively bond or repair the biological tissue. Moreover, the biodegradable sealant of the present disclosure mentioned above can effectively bind or repair biological tissue even in a humid environment. Furthermore, since the biodegradable sealant of the present disclosure mentioned above is not cytotoxic, it has good biocompatibility and does not cause immune response.

In addition, the biodegradable sealant of the present disclosure mentioned above can be naturally catabolized without affecting the repair of the tissue, and can be used as a growth template for cell and tissue repair to accelerate wound healing.

The biodegradable sealant of the present disclosure mentioned above may comprise, but is not limited to, a polyethylene glycol derivative, a photoinitiator and a solvent. In the biodegradable sealant of the present disclosure mentioned above, the content of each component is not particularly limited, and it may be adjusted according to the content of other components, and/or may be adjusted according to requirements.

In one embodiment, in the biodegradable sealant of the present disclosure, the content of the polyethylene glycol derivative may be about 10-75 wt %, such as 15-75 wt %, 20-75 wt %, 10-70 wt %, 35-70 wt %, 35-50 wt %, 40-65 wt %, 40-60 wt %, 40-75 wt %, but it is not limited thereto.

The polyethylene glycol derivative in the biodegradable sealant of the present disclosure may be obtained through a substitution reaction, and in the substitution reaction, polyethylene glycol (PEG) is modified with methacrylic anhydride (MA).

In one embodiment, the molecular weight of the polyethylene glycol used in the substitution reaction may be about 1500-35000, such as about 1500, about 8000, about 35000, but it is not limited thereto.

Moreover, in one embodiment, the weight ratio of the polyethylene glycol used in the foregoing substitution reaction to the methacrylic anhydride used in the foregoing substitution reaction may be about 1:0.01-10, such as about 1:0.05-2, about 1:0.05-1.5, about 1:0.05-1, about 1:0.05-0.5, about 1:1-2, about 1:1-1.5, about 1:0.5-1, about 1:0.5-2 about 1:0.2-2, about 1:0.2-1.5, about 1:0.2-1, about 1:0.1-5, about 1:0.1-4, about 1:0.1-3, about 1:0.1-2, about 1:0.1-1.5, about 1:0.1-1, but it is not limited thereto.

In one specific embodiment, the molecular weight of the polyethylene glycol used in the foregoing substitution reaction may be about 1500, and the weight ratio of the polyethylene glycol used in the foregoing substitution reaction to the methacrylic anhydride used in the substitution reaction may be about 1:1-10, such as about 1:1, 1:2, 1:3, 1:4, but it is not limited thereto. In another embodiment, the molecular weight of the polyethylene glycol used in the foregoing substitution reaction may be about 8000, and the weight ratio of the polyethylene glycol used in the foregoing substitution reaction to the methacrylic anhydride used in the substitution reaction may be about 1:0.05-1.5, such as about 1:0.2 (5:1), about 1:0.384 (2.6:1), about 1:0.588 (1.7:1), about 1:0.769 (1.3:1), about 1:1, but it is not limited thereto. In yet another embodiment, the molecular weight of the polyethylene glycol used in the foregoing substitution reaction may be about 35000, and the weight ratio of the polyethylene glycol used in the foregoing substitution reaction to the methacrylic anhydride used in the substitution reaction may be about 1:0.05-0.8, such as about 1:0.091 (11:1), about 1:0.176 (5.68:1), about 1:0.265 (3.78:1), about 1:0.342 (2.92:1), about 1:0.429 (2.33:1), but it is not limited thereto.

Moreover, in the polyethylene glycol derivative of the biodegradable sealant of the present disclosure, the degree of substitution of the methacrylic anhydride may be about 60-100%, such as about 60-70%, about 70-80%, about 80-90%, about 90-100%, but it is not limited thereto.

The content and type of photoinitiator in the biodegradable sealant of the present disclosure are not particularly limited, as long as the photoinitiator in the biodegradable sealant of the present disclosure can accelerate the solidification of the biodegradable sealant after an illumination procedure is performed on the biodegradable sealant of the present disclosure. The wavelength of the light adopted in the illumination procedure performed on the biodegradable sealant of the present disclosure can depend on the photoinitiator that is used, and the time it takes to perform the illumination procedure mentioned above can depend on the photoinitiator that is used and/or the operating conditions. Furthermore, an example of the photoinitiator may comprise, but is not limited to, a UV photoinitiator.

In one embodiment, in the biodegradable sealant of the present disclosure, the weight ratio of the polyethylene glycol derivative to the photoinitiator may be about 1:0.001-0.01, such as about 1:0.001-0.005, about 1:0.0025-0.01, about 1:0.003-0.006, about 1:0.005-0.01, but it is not limited thereto.

Furthermore, in one embodiment, the photoinitiator mentioned above may be a UV photoinitiator, and the wavelength of the light adopted in the illumination procedure performed on the biodegradable sealant of the present disclosure can depend on the UV photoinitiator that is used, for example, it may be about 200-450 nm, but it is not limited thereto. Examples of the UV photoinitiator may comprise, but are not limited to, riboflavin (the wavelength of UV light suitable for illumination is 220 nm, 261 nm, 376 nm or 439 nm), 2-hydroxy-4'-(2-hydroxyethoxy)-2-methylpropiophenone (the wavelength of UV light suitable for illumination is 276 nm or 331 nm) or phenylbis(2,4,6-trimethylbenzoyl)phosphine oxide (the wavelength of UV light suitable for illumination is 360 nm, 365 nm or 405 nm). Moreover, the time it takes to perform the illumination procedure mentioned above can depend on the UV photoinitiator that is used and/or operating conditions.

The solvent in the biodegradable sealant of the present disclosure is also not particularly limited, as long as it does not adversely affect other components of the sealant and is not cytotoxic. Examples of the solvent in the biodegradable sealant of the present disclosure may comprise water, but it is not limited thereto.

The osmotic pressure of the biodegradable sealant of the present disclosure may be about 300-450 mOsm/kg, such as about 350-450 mOsm/kg, about 300-400 mOsm/kg, about 350-400 mOsm/kg, but it is not limited thereto.

The in vitro degradation time for the biodegradable sealant of the present disclosure may be about 70-90 hours, such as about 70-85 hours, about 75-90 hours, about 75-85 hours, about 75-80 hours, but it is not limited thereto.

In addition, the pH value of the biodegradable sealant of the present disclosure may be about 6.0-7.5, such as about 6.0-7.0, about 6.5-7.5, about 6.5-7.2, but it is not limited thereto.

The present disclosure also provides a use of a biodegradable sealant in the manufacture of an agent for bond or repair of biological tissue, and the biodegradable sealant mentioned herein may be any foregoing biodegradable sealant of the present disclosure.

In the use of a biodegradable sealant in the manufacture of an agent for bond or repair of biological tissue of the present disclosure mentioned above, a method for using the agent for bond or repair of biological tissue may comprise the following steps, but it is not limited thereto. The method for using the agent for bond or repair of biological tissue can be performed in vitro or on a living body.

First, the foregoing agent for bond or repair of biological tissue is applied to a biological tissue to be bonded or repaired. The biological tissue to be bonded or repaired mentioned above may be an ex vivo biological tissue or biological tissue on a living body. The biological tissue to be bonded or repaired may be enumerated as a wound or tissue defect in a subject, but it is not limited thereto.

The subject mentioned above may comprise an animal or a plan. Examples of the animal may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse.

Examples of the wounds or tissue defects in a subject mentioned above may comprise, but are not limited to, skin wounds, surgical wounds, and eye wounds (such as a corneal defect).

Next, an illumination procedure is performed on the foregoing biological tissue to be bonded or repaired to make the agent for bond or repair of biological tissue mentioned above solidify to bond or repair the biological tissue to be bonded or repaired.

The wavelength of the light adopted in the illumination procedure mentioned above can depend on the photoinitiator that is used, and the time it takes to perform the illumination procedure mentioned above can depend on the photoinitiator that is used in the biodegradable sealant of the present disclosure and/or operating conditions. In one embodiment, the time it takes to perform the illumination procedure is about 10-60 seconds, but it is not limited thereto.

In one embodiment, the photoinitiator that is used in the biodegradable sealant of the present disclosure mentioned above may be a UV photoinitiator, and the wavelength of the light adopted in the illumination procedure can depend on the UV photoinitiator that is used, for example, it may be about 200-450 nm, but it is not limited thereto. The time it takes to perform the illumination procedure mentioned above can depend on the photoinitiator that is used in the biodegradable sealant of the present disclosure and/or operating conditions, for example, it may be about 10-60 seconds, but it is not limited thereto. Examples of the UV photoinitiator may comprise, but are not limited to, riboflavin (the wavelength of UV light suitable for illumination is 220 nm, 261 nm, 376 nm or 439 nm), 2-hydroxy-4'-(2-hydroxyethoxy)-2-methylpropiophenone (the wavelength of UV light suitable for illumination is 276 nm or 331 nm) or phenylbis(2,4,6-trimethylbenzoyl)phosphine oxide (the wavelength of UV light suitable for illumination is 360 nm, 365 nm or 405 nm).

In one specific embodiment, the biological tissue to be bonded or repaired mentioned above is a skin wound in a subject, and the molecular weight of the polyethylene glycol used in the substitution reaction for forming the polyethylene glycol derivative in the biodegradable sealant of the present disclosure mentioned above is about 35000.

In another specific embodiment, the biological tissue to be bonded or repaired mentioned above is an eye wound in a subject, and the molecular weight of the polyethylene glycol used in the substitution reaction for forming the polyethylene glycol derivative in the biodegradable sealant of the present disclosure mentioned above is about 8000.

EXAMPLES

Example 1: Preparation of Polyethylene Glycol Derivative

Example 1-1: Preparation of Polyethylene Glycol 1500 Modified with Methacrylic Anhydride The synthesis of methacrylic anhydride modified polyethylene glycol 1500 was performed, based on the following steps, by the refluxing and dropping reaction device 100 (with magnetic stirrer S) shown in FIG. 1.

1. 10 g of polyethylene glycol (molecular weight 1500) (hereinafter referred to as polyethylene glycol 1500) was added to a separate, unassembled 250 mL flask C, heated to 120° C., and dewatered through air-bleed by a pump connected to flask C for 8 hours. After that, the polyethylene glycol 1500 which had been treated as described above was ready for use.

2. Assembly of the refluxing and dropping reaction device 100 was completed, and a nitrogen gas dehydrated by a desiccant was introduced to the refluxing and dropping reaction device 100 to fill the entire device with nitrogen gas.

3. The polyethylene glycol 1500 in flask C of step 1 was dissolved with 100 mL tetrahydrofuran.

4. 10.3 g methacrylic anhydride was dissolved with 50 mL tetrahydrofuran to form a solution, and the solution was added to flask A.

5. Flask C was heated to 80° C., and condensing reflux device B was turned on.

6. The solution in flask A was slowly dropped into flask C for reacting for 8 hours.

7. After the reaction was completed, the product was poured to 1000 mL ether to perform precipitation.

8. Suction filtration was performed on the product of step 7. After that, the upper solid was taken and dissolved by heating in 50 mL tetrahydrofuran, and then was precipitated by ether. This step was repeated 3 times.

9. Finally, the product of step 8 was vacuum-dried for more than 1 hour. After that, the dried product was placed overnight in a chemical hood for drying to obtain methacrylic anhydride modified polyethylene glycol 1500 (PEGMA1500).

Example 1-2: Preparation of Polyethylene Glycol 8000 Modified with Methacrylic Anhydride Example 1-2-1: Preparation of Polyethylene Glycol 8000 Modified with Methacrylic Anhydride (the Molar Ratio of Polyethylene Glycol 8000 to Methacrylic Anhydride which was Adopted was 1:5)

The synthesis of methacrylic anhydride modified polyethylene glycol 8000 was performed, based on the following steps, by the refluxing and dropping reaction device 100 (with magnetic stirrer S) shown in FIG. 1.

1. 10 g of polyethylene glycol (molecular weight 8000) (hereinafter referred to as polyethylene glycol 8000) was added to a separately unassembled 250 mL flask C, heated to 120° C., and dewatered through air-bleed by a pumping pump connected to flask C for 8 hours. After that, the polyethylene glycol 8000 which had been treated as described above was ready for use.

2. Assembly of the refluxing and dropping reaction device 100 was completed, and a nitrogen gas dehydrated by a desiccant was introduced to the refluxing and dropping reaction device 100 to fill the entire device with nitrogen gas.

3. The polyethylene glycol 8000 in flask C of step 1 was dissolved with 100 mL tetrahydrofuran.

4. 1.9 g methacrylic anhydride was dissolved with 20 mL tetrahydrofuran to form a solution, and the solution was added to flask A.

5. Flask C was heated to 80° C., and condensing reflux device B was turned on.

6. The solution in flask A was slowly dropped into flask C for reacting for 8 hours.

7. After the reaction was completed, the product was poured to 1000 mL ether to perform precipitation.

8. Suction filtration was performed on the product of step 7. After that, the upper solid was taken and dissolved by heating in 50 mL tetrahydrofuran, and then was precipitated by ether. This step was repeated 3 times.

9. Finally, the product of step 8 was vacuum-dried for more than 1 hour. After that, the dried product was placed overnight in a chemical hood for drying to obtain methacrylic anhydride modified polyethylene glycol 8000 (PEGMA8000).

Example 1-2-2: Preparation of Polyethylene Glycol 8000 Modified with Methacrylic Anhydride (the Molar Ratio of Polyethylene Glycol 8000 to Methacrylic Anhydride which was Adopted was 1:2)

Except for using 10 g of polyethylene glycol 8000 and 0.77 g of methacrylic anhydride being different from Example 1-2-1, other steps were the same as those in Example 1-2-1.

Example 1-2-3: Preparation of Polyethylene Glycol 8000 Modified with Methacrylic Anhydride (the Molar Ratio of Polyethylene Glycol 8000 to Methacrylic Anhydride which was Adopted was 1:10)

Except for using 10 g of polyethylene glycol 8000 and 3.85 g of methacrylic anhydride being different from Example 1-2-1, other steps were the same as those in Example 1-2-1.

Example 1-3: Preparation of Polyethylene Glycol 35000 Modified with Methacrylic Anhydride Example 1-3: Preparation of Polyethylene Glycol 35000 Modified with Methacrylic Anhydride (the Molar Ratio of Polyethylene Glycol 35000 to Methacrylic Anhydride which was Adopted was 1:10)

The synthesis of methacrylic anhydride modified polyethylene glycol 35000 was performed, based on the following steps, by the refluxing and dropping reaction device 100 (with magnetic stirrer S) shown in FIG. 1.

1. 10 g of polyethylene glycol (molecular weight 35000) (hereinafter referred to as polyethylene glycol 35000) was added to a separately unassembled 250 mL flask C, heated to 120° C., and dewatered through air-bleed by a pumping pump connected to flask C for 8 hours. After that, the polyethylene glycol 35000 which had been treated as described above was ready for use.

2. Assembly of the refluxing and dropping reaction device 100 was completed, and a nitrogen gas dehydrated by a desiccant was introduced to the refluxing and dropping reaction device 100 to fill the entire device with nitrogen gas.

3. The polyethylene glycol 35000 in flask C of step 1 was dissolved with 100 mL tetrahydrofuran.

4. 0.88 g methacrylic anhydride was dissolved with 10 mL tetrahydrofuran to form a solution, and the solution was added to flask A.

5. Flask C was heated to 80° C., and condensing reflux device B was turned on.

6. The solution in flask A was slowly dropped into flask C for reacting for 8 hours.

7. After the reaction was completed, the product was poured to 1000 mL ether to perform precipitation.

8. Suction filtration was performed on the product of step 7. After that, the upper solid was taken and dissolved by heating in 50 mL tetrahydrofuran, and then was precipitated by ether. This step was repeated 3 times.

9. Finally, the product of step 8 was vacuum-dried for more than 1 hour. After that, the dried product was placed overnight in a chemical hood for drying to obtain methacrylic anhydride modified polyethylene glycol 35000 (PEGMA35000).

Comparative Example 1-3-1: Preparation of Polyethylene Glycol 35000 Modified with Methacrylic Anhydride (the Molar Ratio of Polyethylene Glycol 35000 to Methacrylic Anhydride which was Adopted was 1:2)

Except for using 10 g of polyethylene glycol 35000 and 0.088 g of methacrylic anhydride being different from Example 1-3, other steps were the same as those in Example 1-3.

Comparative example 1-3-2: Preparation of polyethylene glycol 35000 modified with methacrylic anhydride (the molar ratio of polyethylene glycol 35000 to methacrylic anhydride which was adopted was 1:5)

Except for using 10 g of polyethylene glycol 35000 and 0.44 g of methacrylic anhydride being different from Example 1-3, other steps were the same as those in Example 1-3.

Example 2: Confirmation of Whether Methacrylic Anhydride Modified Polyethylene Glycol was Successfully Synthesized Example 2-1: Confirmation of Whether Methacrylic Anhydride Modified Polyethylene Glycol 8000 was Successfully Synthesized NMR spectrum analysis was performed on the products of Example 1-2-1, Example 1-2-2 and Example 1-2-3, and the results are shown in FIGS. 2A, 2B and 2C, respectively.

Figure 2A:
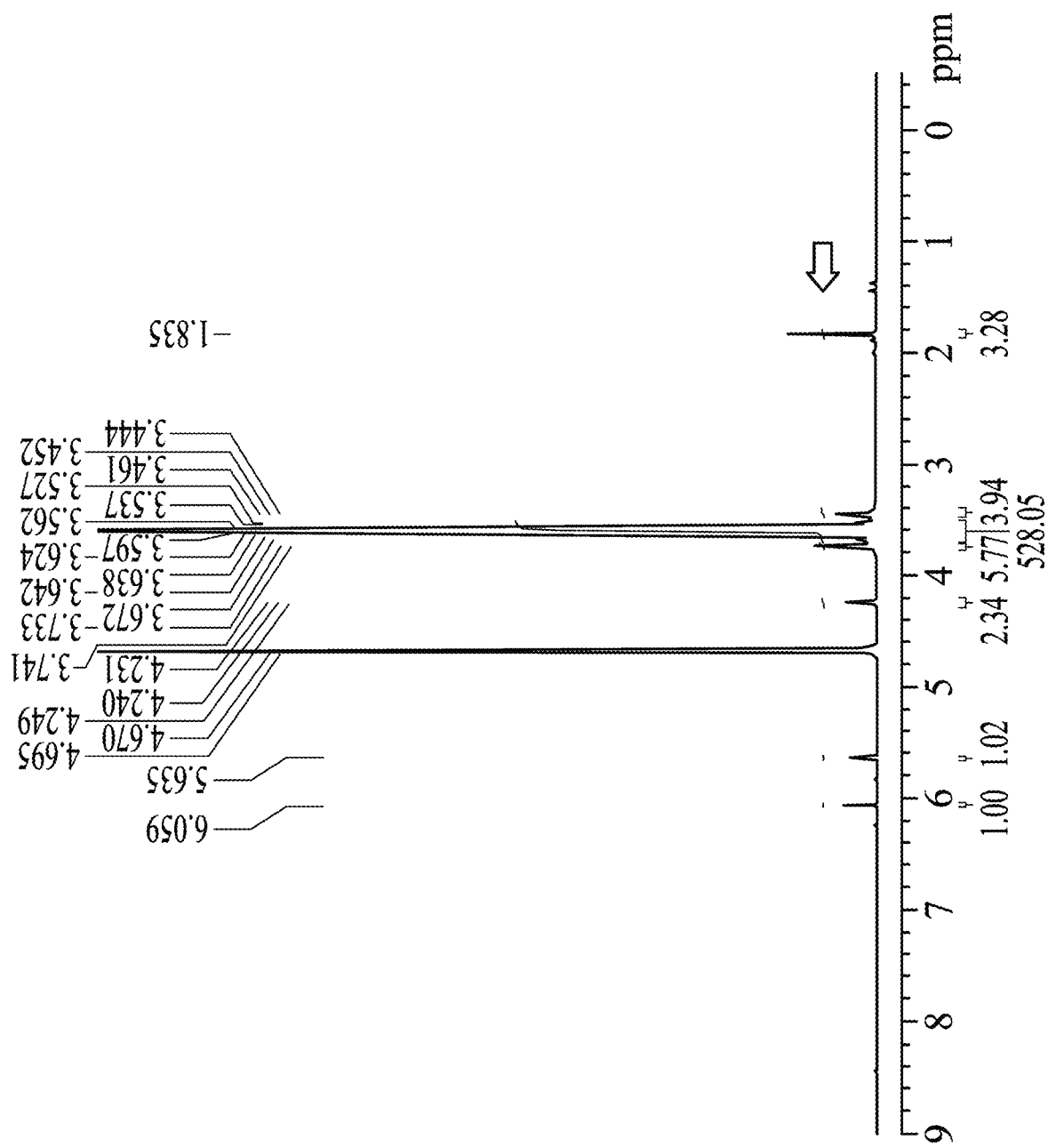
FIG. 2A shows the result of NMR spectrum analysis of the product of Example 1-2-1 of the present disclosure.
Figure 2B:
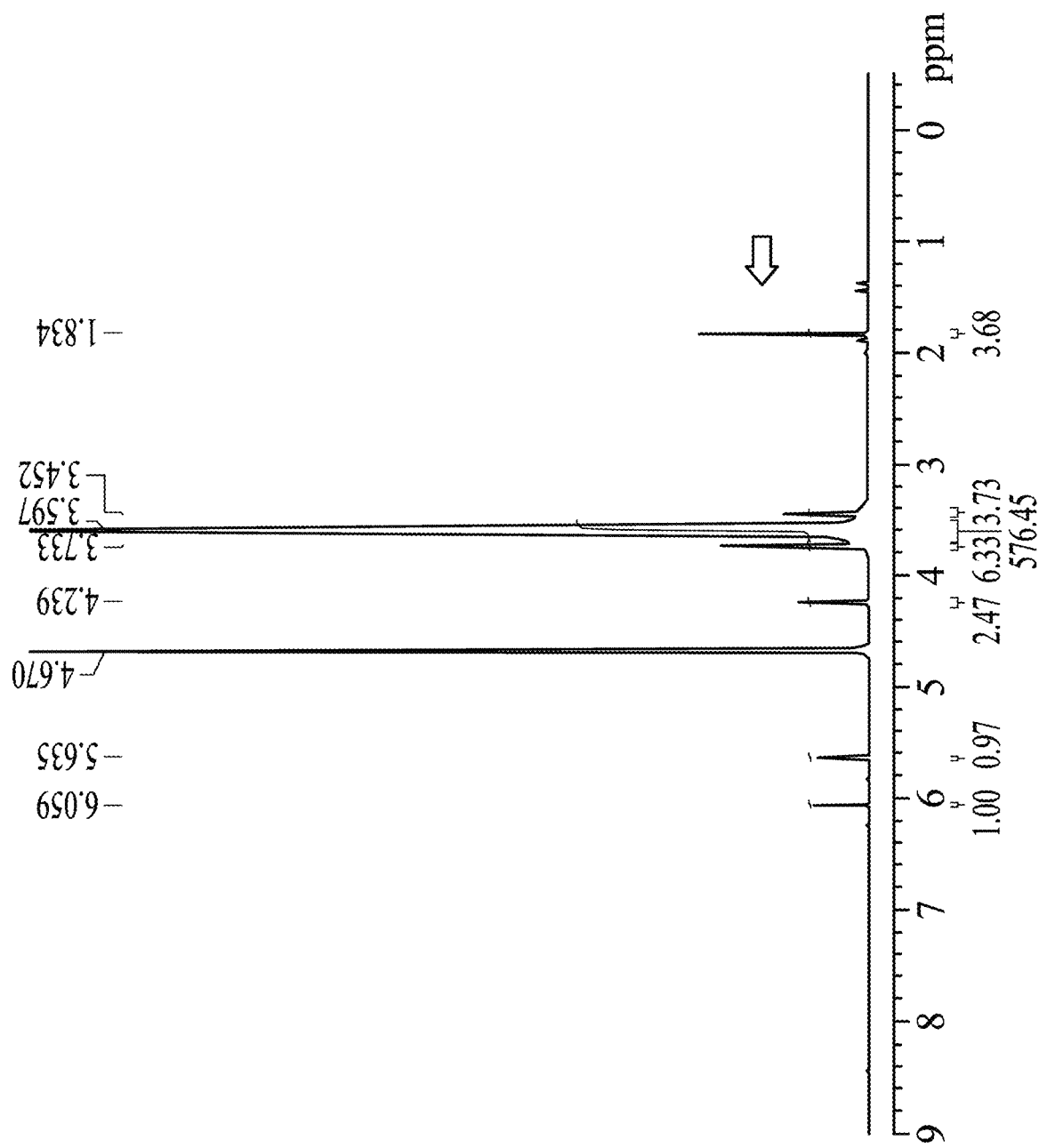
FIG. 2B shows the result of NMR spectrum analysis of the product of Example 1-2-2 of the present disclosure.
Figure 2C:
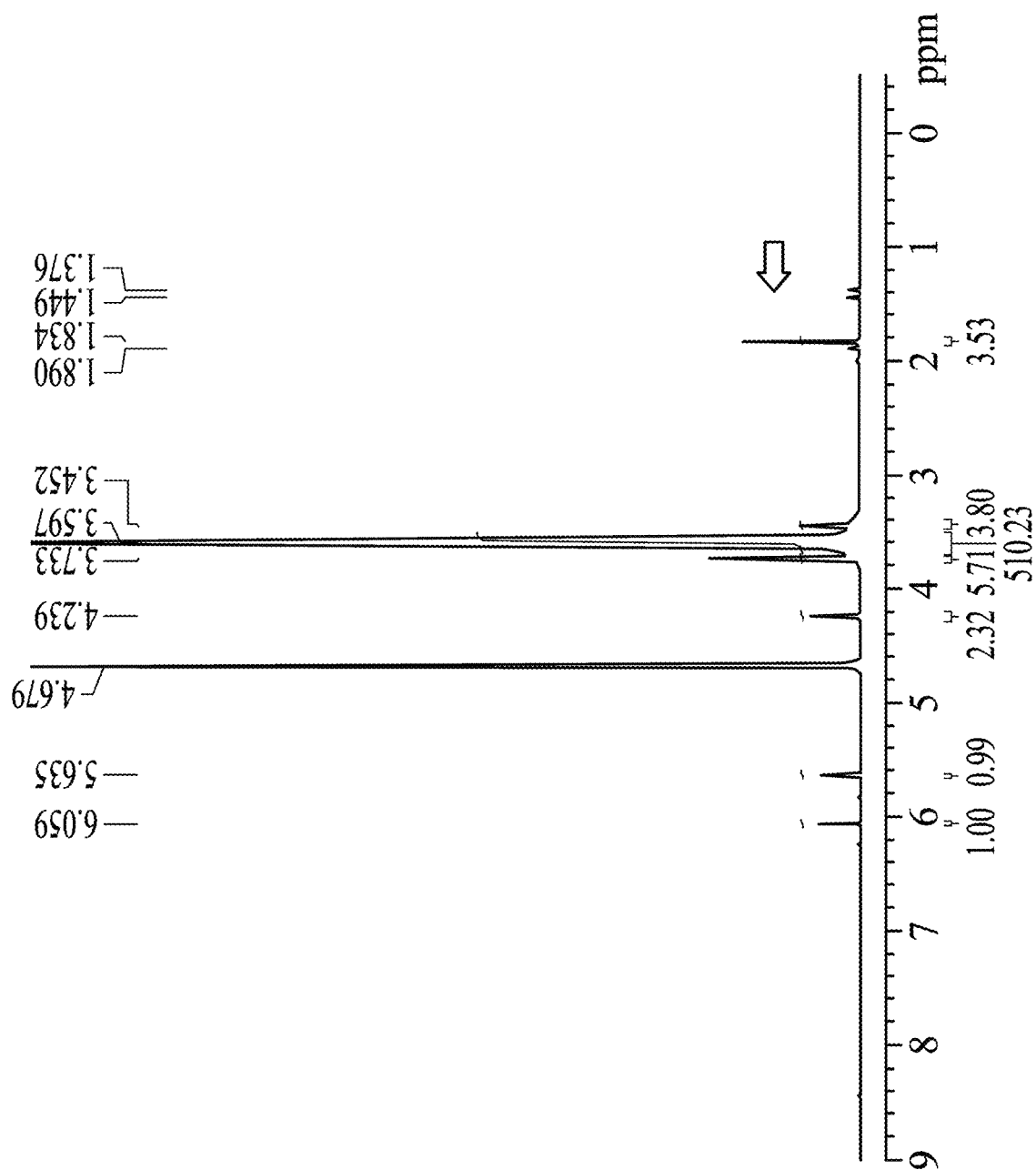
FIG. 2C shows the result of NMR spectrum analysis of the product of Example 1-2-3 of the present disclosure.

According to the NMR spectra shown in FIGS. 2A, 2B, and 2C, it is known that the products of Example 1-2-1, Example 1-2-2, and Example 1-2-3 all have a peak indicated by an arrow. This peak represents the successful grafting of methacrylic anhydride to polyethylene glycol 8000, namely that the methacrylic anhydride modified polyethylene glycol 8000 was successfully synthesized.

Based on the results mentioned above, it is understood that when the molecular weight of the polyethylene glycol used in the synthesis is 8000, the effect of the molar ratio of the polyethylene glycol to the methacrylic anhydride is not significant for the success of the synthesis.

Furthermore, confirmation of degrees of substitution of methacrylic anhydride of the products of Example 1-2-1, Example 1-2-2 and Example 1-2-3 was performed, and the results showed that degrees of substitution of methacrylic anhydride of the products of Example 1-2-1, Example 1-2-2 and Example 1-2-3 were about 60-70%.

Example 2-2: Confirmation of Whether of Methacrylic Anhydride Modified Polyethylene Glycol 35000 was Successfully Synthesized NMR spectrum analysis was performed on the products of Comparative example 1-3-1, Comparative example 1-3-2 and Example 1-3, and the results are shown in FIGS. 3A, 3B and 3C, respectively.

Figure 3A:
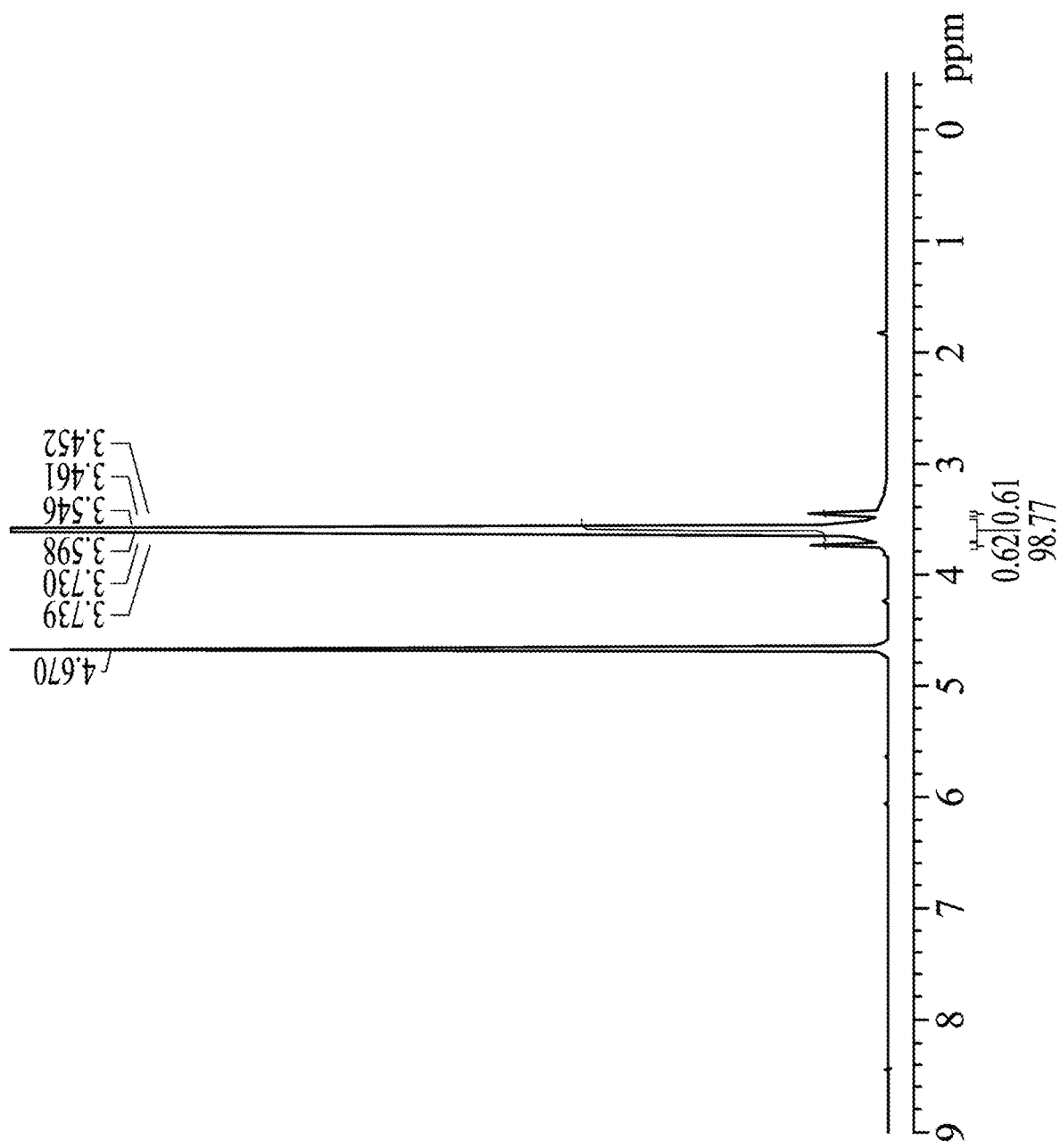
FIG. 3A shows the result of NMR spectrum analysis of the product of Comparative Example 1-3-1 of the present disclosure.
Figure 3B:
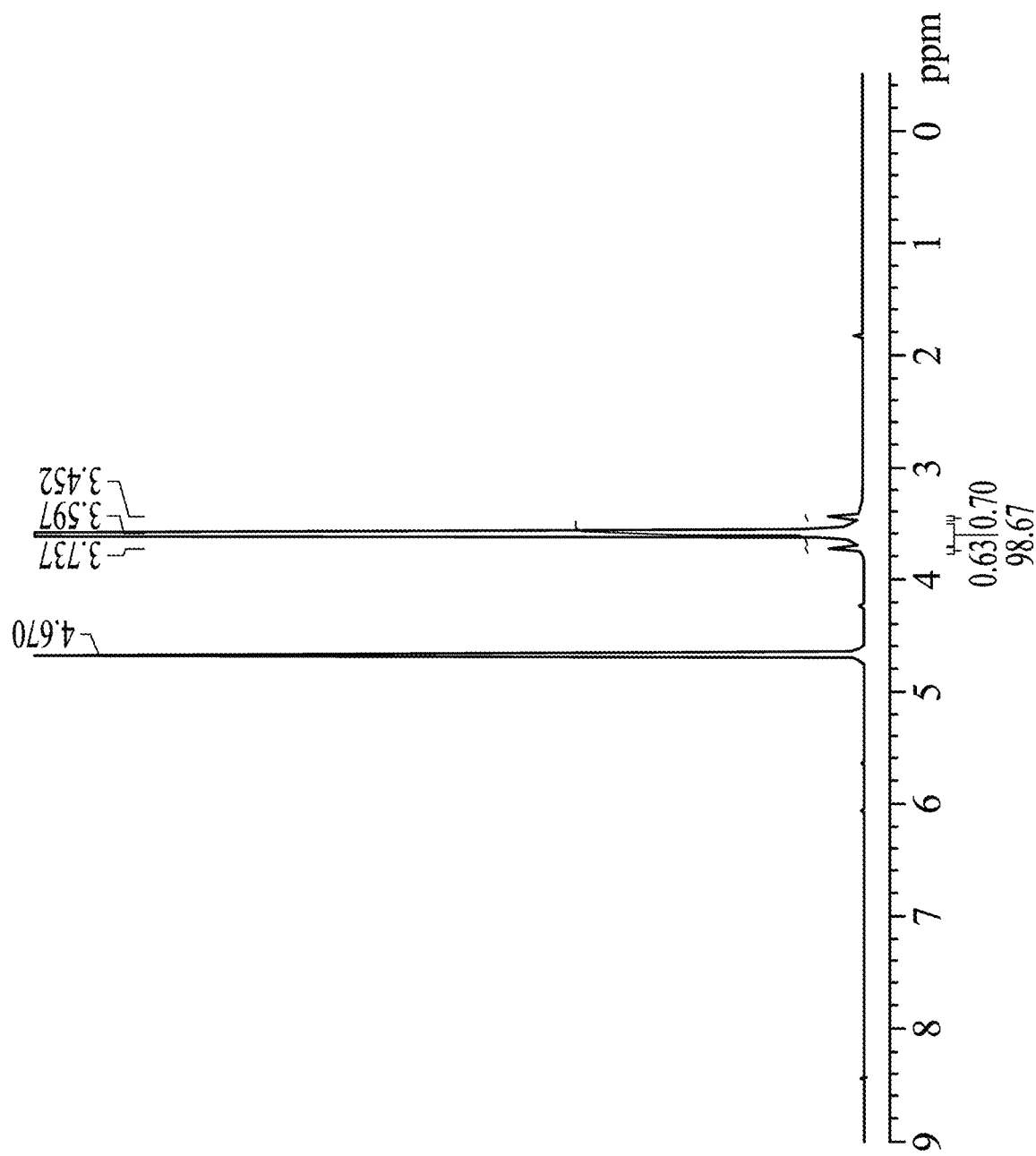
FIG. 3B shows the result of NMR spectrum analysis of the product of Comparative Example 1-3-2 of the present disclosure.
Figure 3C:
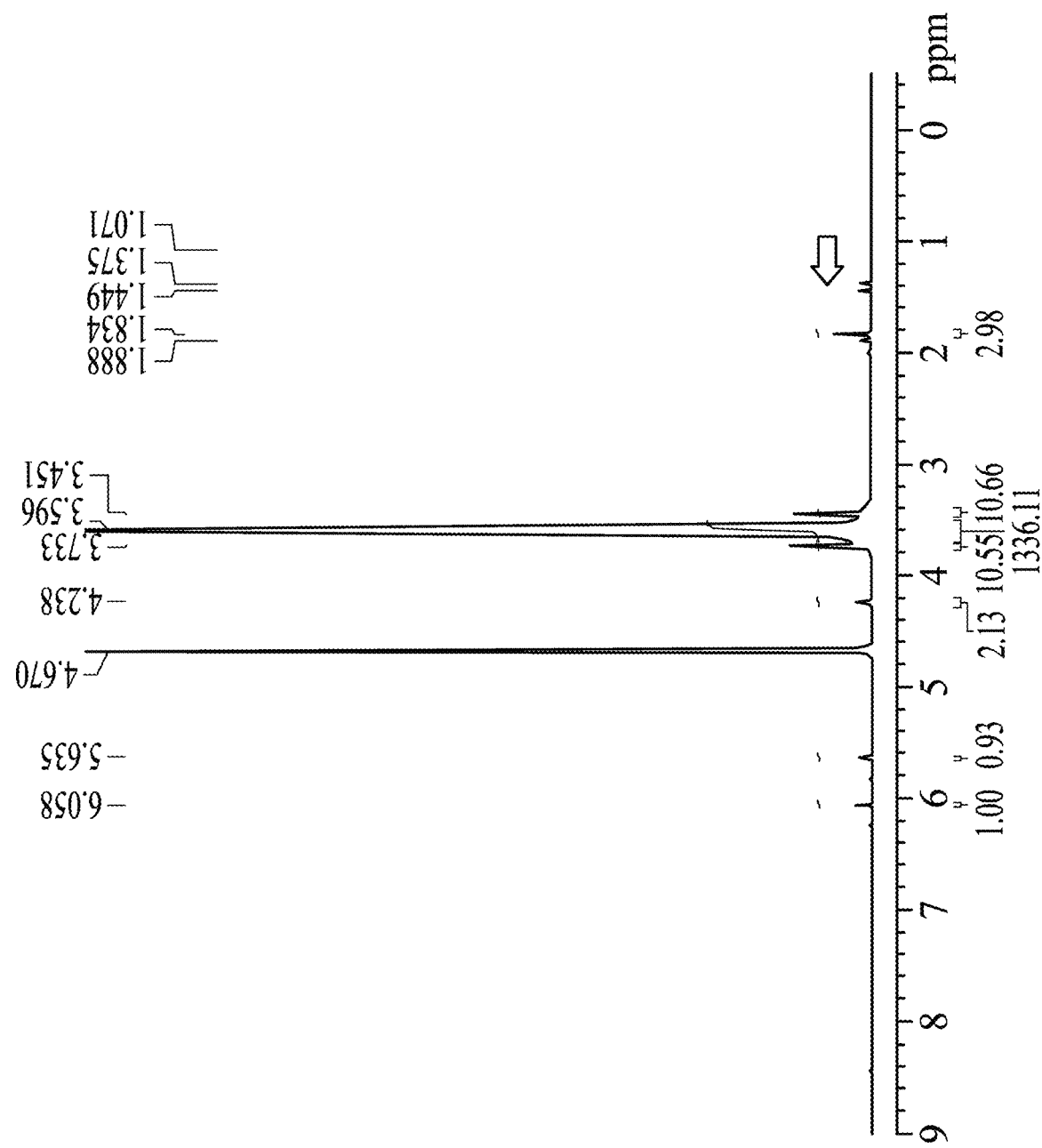
FIG. 3C shows the result of NMR spectrum analysis of the product of Example 1-3 of the present disclosure.

According to the NMR spectra shown in FIGS. 3A, 3B, and 3C, it is known that only the product of Example 1-3 has a peak indicated by an arrow. This peak represents the successful grafting of methacrylic anhydride to polyethylene glycol 35000, namely that the methacrylic anhydride modified polyethylene glycol 35000 was successfully synthesized.

Based on the results mentioned above, it is understood that when the molecular weight of the polyethylene glycol used in the synthesis is 35000, the effect of the molar ratio of the polyethylene glycol to the methacrylic anhydride is more significant for the success of the synthesis, and polyethylene glycol 35000 modified with methacrylic anhydride was successfully synthesized only when the molar amount of methacrylic anhydride was 10-times that of polyethylene glycol.

Furthermore, confirmation of degrees of substitution of methacrylic anhydride of the product of Example 1-3 was performed, and the results showed that degree of substitution of methacrylic anhydride of the products of Example 1-3 could reach to about 100%.

Example 3: Preparation of Sealant

Based on the different formulations shown in the following Table 1, the ingredients were mixed directly to prepare sealants with different formulations, separately.

TABLE 1

|  | PEGMA 1500 (g) | PEGMA 8000 (prepared by Example 1-2-2) (g) | PEGMA 35000 (g) | Initiator (g) | Solvent (g) | PEGMA content (wt %) |
| --- | --- | --- | --- | --- | --- | --- |
| Sealant 1 | 400 | — | — | 1 | 100 | about 80% |
| Sealant 2 | 66.66 | — | — | 1 | 100 | about 40% |
| Sealant 3 | 25 | — | — | 1 | 100 | about 20% |
| Sealant 4 | — | 300 | — | 1 | 200 | about 60% |
| Sealant 5 | — | 66.66 | — | 1 | 100 | about 40% |
| Sealant 6 | — | — | 175 | 1 | 325 | about 35% |
| Sealant 7 | — | — | 50 | 1 | 200 | about 20% |
| Sealant 8 | — | — | 35.3 | 1 | 200 | about 15% |

Figure 4:
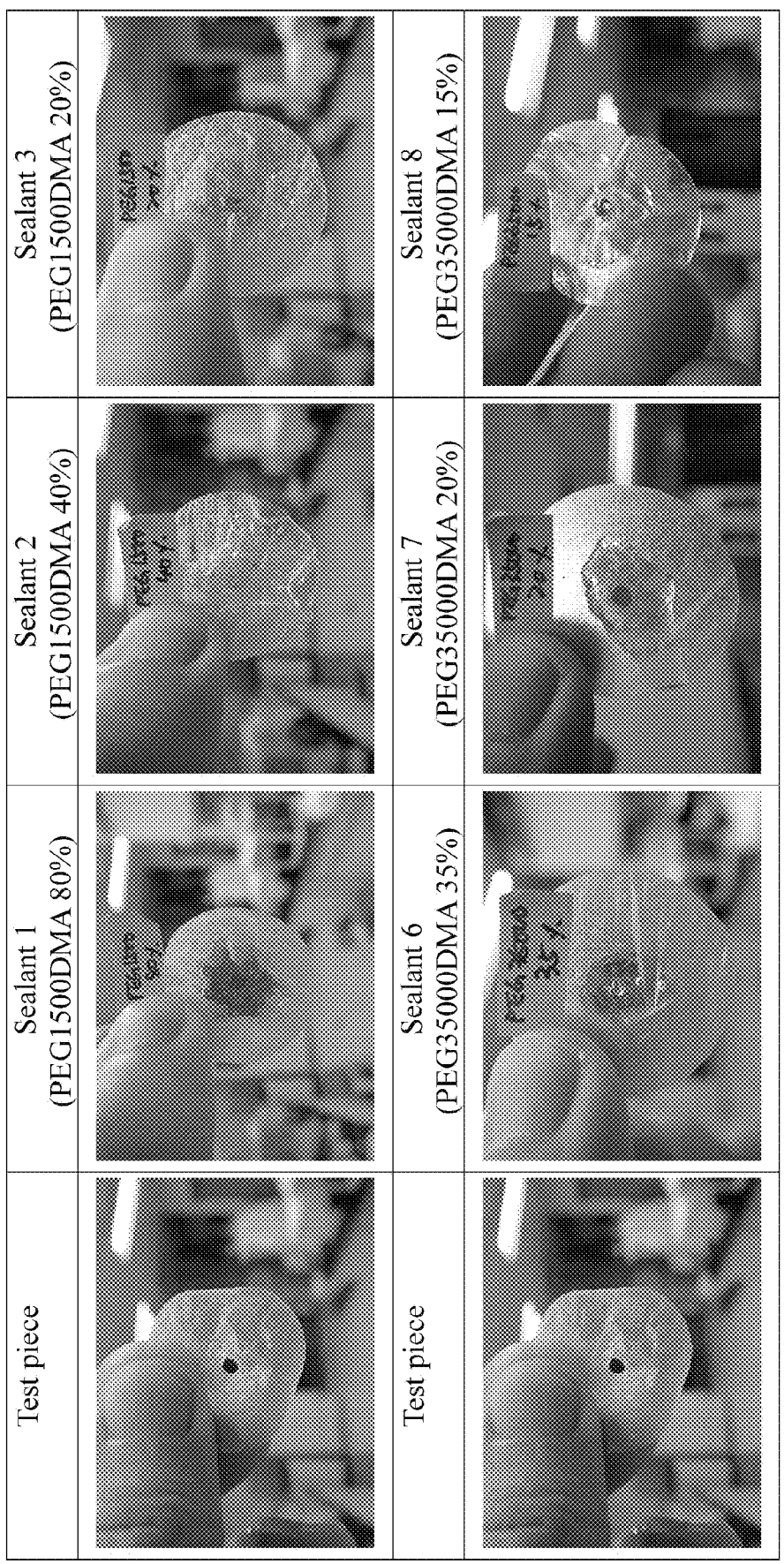
FIG. 4 shows a photograph of the sealants of the different formulations of the present disclosure which are cured after bonding to the test pieces (the membranes of pork intestine)

Initiator: 2-hydroxy-4'-(2-hydroxyethoxy)-2-methylpropiophenone; solvent: water; -: No addition Example 4: Evaluation of the Preliminary Appearance and Properties of the Sealants The sealants with different formulations prepared in Example 3 were irradiated with a UV lamp for 60 seconds to cure them. After that, preliminary appearance and property evaluation was performed on the cured sealants with different formulations, and the results are shown in Table 2 and FIG. 4

TABLE 2

| | Evaluation result |
|---|---|
| Sealant 1 (PEGMA1500 content: about 80%) | After curing, it had high strength, had low toughness and was brittle, and that might cause foreign body sensation. |
| Sealant 2 (PEGMA1500 content: about 40%) | The performance was the same as that of the Sealant 1, and since the concentration therein was low, the fluidity thereof increased. It is suitable for bonding of different tissues. |
| Sealant 3 (PEGMA1500 content: about 20%) | The performance was the same as that of the sealant 1, and since the concentration therein was lower, the fluidity thereof increased. It is suitable for situations where a large area of bonding is required. |
| Sealant 4 (PEGMA8000 content: about 60%) | After curing, it had moderate strength, had toughness, and could attach to the tissue well. |
| Sealant 5 (PEGMA8000 content: about 40%) | It was transparent and was capable of quickly bonding the bonding target. It is suitable for ophthalmology, does not hinder sight, and the foreign body sensation is low. |
| Sealant 6 (PEGMA35000 content: about 35%) | After curing, it had low strength. It is suitable for soft tissues. |
| Sealant 7 (PEGMA35000 content: about 20%) | The performance was the same as that of the sealant 6, and since in that the concentration was lower, the fluidity thereof increased. It is suitable for situations where a large area of bonding is required. |
| Sealant 8 (PEGMA35000 content: about 15%) | The performance was the same as that of the sealant 6, and since in that the concentration was lower, the fluidity thereof increased, the viscosity increased. |

According to Table 2, it is known that Sealant 2 has better operability.

Example 5: Evaluation of Physical and Chemical Properties of Sealant

Sealant 4 of the present disclosure prepared in Example 3 and a commercial product (Resure) were evaluated for various physical and chemical properties. The evaluation methods and results are shown in Table 3.

TABLE 3

| | Description of test | Sealant of the present disclosure | Resure |
|---|---|---|---|
| Mixing time | — | Directly use without mixing | <5 seconds |
| Gel time | Use a timer to count, and after every second of illumination, visually confirm whether the sample will continue to flow. | 10 seconds | 14.39-17.82 seconds |
| Pot life (The product can be used after opening) | After a sample being opened, every 5 minutes observe whether the sample solidify into a colloid. | More than or equal to 30 minutes | 30 minutes |
| Swelling | Weigh a dried sample. After that, place the sample in a 37° C. PBS buffer solution. After 2.5 hours, take the sample out, and dry the sample with paper and weigh the sample. Calculate the percentage increase in weight of the sample. | 50.6% (Before swelling: 85.7 mg; after swelling: 173.5 mg) 51.3% (Before swelling: 91 mg; after swelling: 186.9 mg) 52.1% (Before swelling: 92.6 mg; after swelling: 193.5 mg) | 35.6% |
| Burst strength | Irradiate a product with light to cure the product on a flaky pig intestinal membrane (outer diameter 35 mm:inner diameter 2.5 mm) for a burst test. Test a sample by applying various liquid pressures which are set to determine the pressure at which the sample and the intestinal membrane suddenly rupture. | 183.018 mmHg | 67 mmHg |
| pH | Directly detect a sample by a pH meter. | 6.7 | 6.524 |
| Osmolality | Directly detect a sample by an osmometer. | 381 mOsm/kg | 271.8 mOsm/kg |
| Heat generation during polymerization | Irradiate an application site with light, and directly determine whether the sample absorbs heat during polymerization on the skin. | No significant temperature changes on the skin | No significant temperature changes on the skin |

TABLE 3-continued

| Description of test | | Sealant of the present disclosure | Resure |
|---|---|---|---|
| In vitro persistence | Weigh a sample after drying. After that, place the sample in a 37° C. PBS buffer solution. Take the sample out from the PBS buffer solution at each set time point and weigh dry the sample with paper and weigh the sample until the sample is dissolved in the PBS buffer solution. | 75-80 hours | 81 hours |

Example 6: Swelling Studies and Degradation Analysis

A. Methods

The samples (Sealant 4 prepared by Example 3) were placed in a vacuum oven at 37° C. for 24 hours, and then their apparent dry weights (Wd) were measured. The samples were then placed in distilled water to determine their water uptake (Ws) after drying at 37° C.

Mass loss was measured using a balance. At each time point, the samples were weighed after drying, and mass loss was calculated by comparing the initial mass with that at a given time point. Measurements were performed while maintaining the samples at 3 temperatures, 37° C., 50° C., and 65° C. and the results are presented as the mean.

B. Results

Figure 5A:
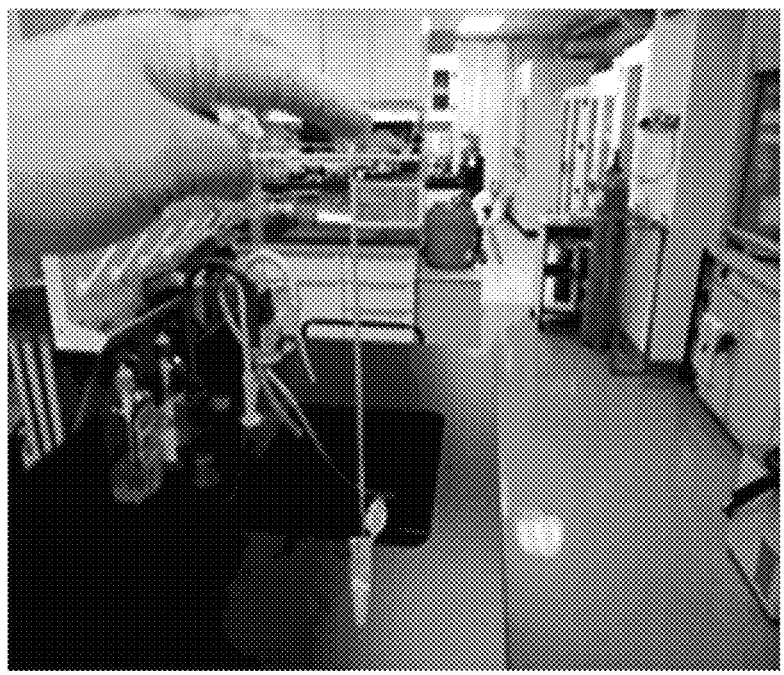
FIG. 5A shows a photograph of the elasticity of the sealant of the present disclosure. The sealant can easily be stretched to about 10 times its original length without visible or permanent deformation.
Figure 5B:
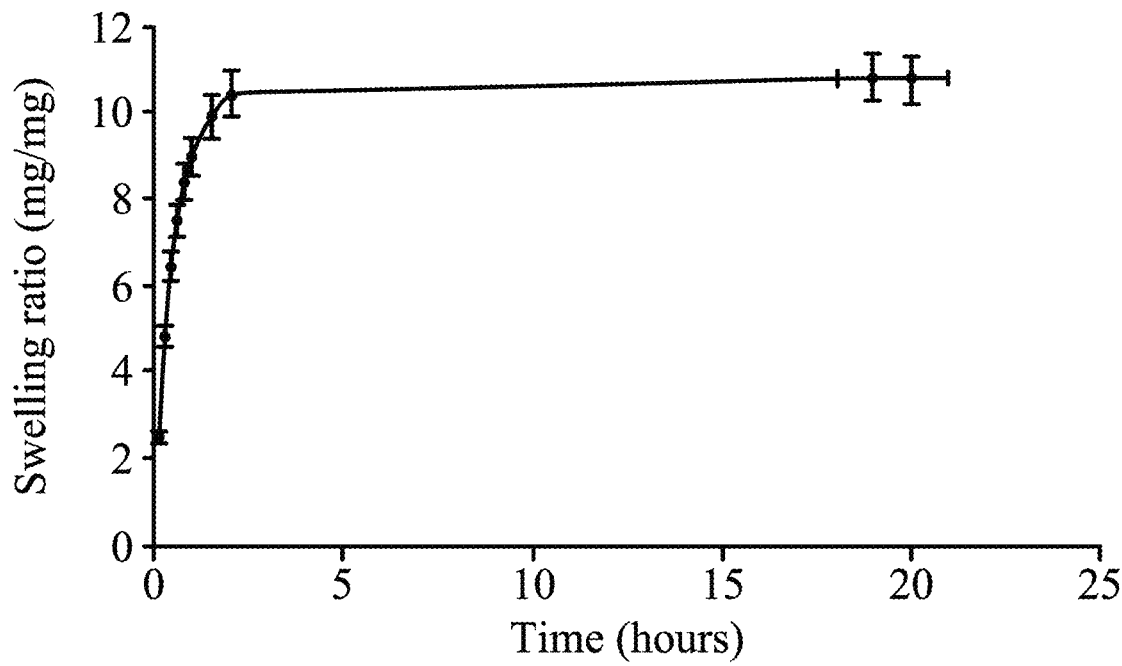
FIG. 5B shows the swelling ratios of the sealant of the present disclosure at different time points.

FIG. 5A presents the adhesion and stretching results of a line-shaped hydrogel attached to a 1.5 mL microcentrifuge tube. The elongated sealant adhered easily to skin even when part of it was removed. FIG. 5B shows the sealant of the present disclosure before and after immersion in water. The sealant of the present disclosure swelled to 11-times its initial weight in the first 2 hours (FIG. 5B).

Figure 5C:
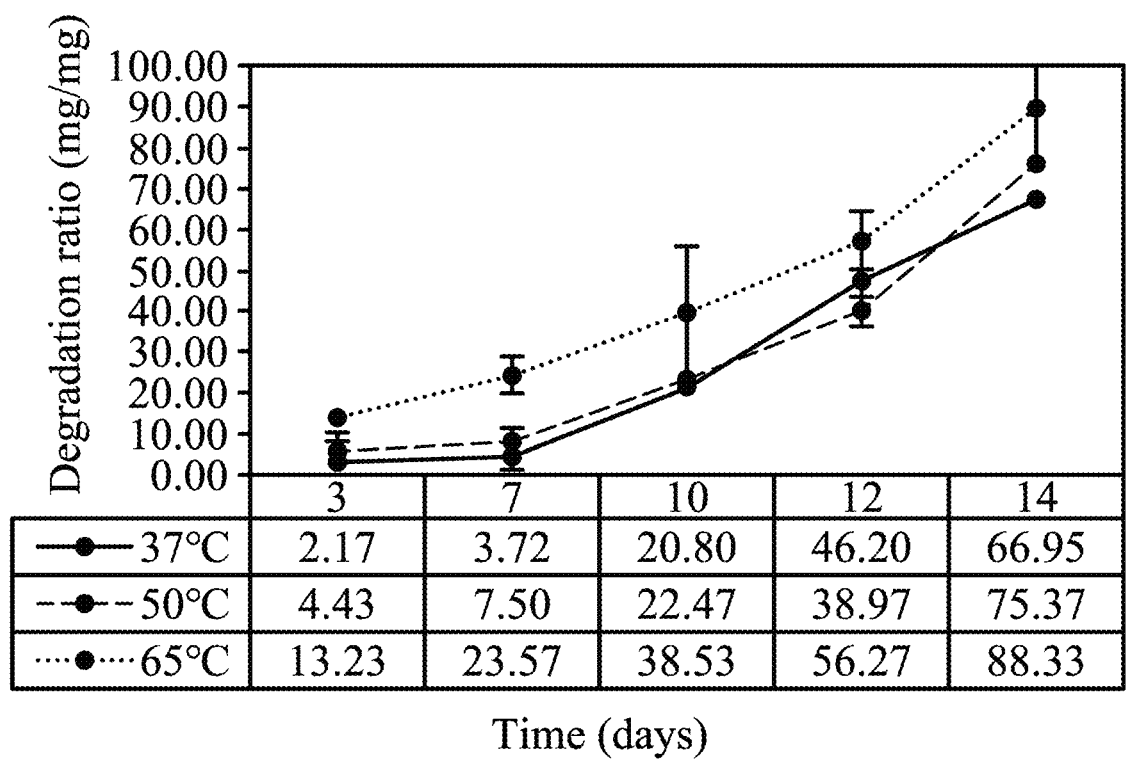
FIG. 5C shows that the relative mass of the sealant of the present disclosure decreases with time due to the decrease in the temperature difference.

The mass loss data for the sealant of the present disclosure degraded at temperatures of 37° C., 50° C., and 65° C. are summarized in FIG. 5C. During the first 3 days, similar mass losses were observed for the sealants maintained at temperatures of 37° C. and 50° C. At Day 7, samples maintained at a temperature of 65° C. exhibited faster rates of mass loss, losing a total of 20% of their original mass. At Day 14, samples maintained at 65° C. showed a faster mass loss rate at Day 12 of degradation, losing more than 95% of their original weight. The mass loss rate of the sealant of the present disclosure maintained at 65° C. was higher than those of the sealant of the present disclosures maintained at 37° C. and 50° C.

Example 7: Biological Property Test for Sealant of the Present Disclosure

A. Methods

1. Cytotoxicity Analysis and 3-(4,5-dimethyl-thiazol-2-yl)-2,5-diphenyltetrazolium (MTT) Assay In this assay, Sealant 4 prepared by Example 3 was adopted.

The cytotoxicity analysis was performed according to ISO 10993-5:2009. Using a mouse fibroblast cell line (L929; Bioresources Collection and Research Center, Hsin Chu, Taiwan), qualitative measures of cell morphology and monolayer confluency were scored under a microscope.

Cryopreserved L929 cells were thawed and cultured in minimum essential media/alpha modification medium (Invitrogen, Carlsbad, Calif., USA) at 37±1° C. in a 5% $CO_2$ atmosphere. When the cell monolayer reached 80% confluency as assessed with a microscope, the cells were subcultured until reaching passage 2 or 3 prior to use. The culture medium was replaced twice a week. According to ISO 10993-12, the surface ratio of the test compound/culture medium was 0.2 g/mL. Accordingly, 3.6 g of each test sample (S) was extracted with 18 mL of culture medium at a rotation speed of 1,000 g at 37±1° C. for 24±2 hours. A 10% (v/v) solution of dimethyl sulfoxide (DMSO Sigma-Aldrich) prepared using culture medium was used as the positive control (PC). Based on ISO 10993-12, the extraction ratio was 0.2 g/mL, and 1.0 g of high-density polyethylene (Sigma-Aldrich) was used as a negative control (NC). Each sample was immersed in 5 mL of culture medium and extracted at a rotation speed of 1,000 g at 37±1° C. for 24±2 hours. In addition, 5 mL of culture medium was used as a blank (B) and then incubated at a rotation speed of 100 rpm at 37±1° C. for 24±2 hours.

The MTT (Sigma-Aldrich) assay was performed to quantitatively assess the cytotoxicity of the test sample extracts. For the assay, $5 \times 10^4$ L929 mouse fibroblast cells were seeded in 24-well culture plates and then incubated at 37±1° C. in a 5% $CO_2$ atmosphere for 24±2 hours to obtain confluent cell monolayers. After cell attachment, the original culture medium in each well was removed and replaced with 0.5 mL of the respective test medium (B, PC, NC, and S). Then, the test plates were incubated at 37±1° C. in a 5% $CO_2$ atmosphere for 24±2 hours. The plate was incubated for 24 hours. After 24 hours, the cells in each well were stained with neutral red solution (Sigma-Aldrich) and scored according to the change in cell morphology and viability under an inverted microscope (Carl Zeiss MicroImaging GmbH, Göttingen, Germany) in accordance with the criteria in Table 4. At the end of the incubation period, 10 mL of MTT reagent was added to each well, which contained 100 mL of medium. The reaction was performed at 37° C. in a 5% $CO_2$ atmosphere for 2 hours in the dark. Then, 0.1 mL of detergent reagent (Sigma-Aldrich) was added to each well followed by incubation in the dark for 2 hours, after which the absorbance was measured. The absorbance of test samples was measured at 570 nm (reference wavelength: 630 nm) with a microplate reader (Molecular Devices, Silicon Valley, Calif., USA).

TABLE 4

Cytotoxicity Evaluated Using Neutral Red Stain.

| Test Item | Cell Lysis | Grade |
|---|---|---|
| Blank (B) | 0 | 0 |
| Negative control (NC) | 1 | 0 |
| Positive control (PC) | 100 | 4 |
| Test sample (S) | 5 | 0 |

2. Skin Sensitization Study

In this study, Sealant 4 prepared by Example 3 was adopted.

For the study to comply with the "Good Laboratory Practice for Nonclinical Laboratory Study," quality assurance unit audited the facility, equipment, personnel, test methods, raw data, and records regularly. All animal experiments were conducted according to a protocol approved by Master Laboratory CO., Ltd (IACUC No.: MS20160706, Hsinchu County, Taiwan, People's Republic of China). The skin sensitization potential of the extracts of the sealant of the present disclosure (the polar extract was extracted with 60% 2,4-Dinitrochlorobenzene (DNCB) while the non-polar extract was extracted with cottonseed oil) was tested on guinea pigs (body weights (BWs) [gender]: 300 to 500 g [male]; age: around 85 days, from the National Laboratory Animal Center, Taiwan) following ISO 10993-10: 2010. After treatment with the test compound (polar and nonpolar extracts of the sealant of the present disclosure), the extracts were applied twice in the induction phase and once in the challenge phase. Then, 24 hours and 48 hours after the challenge phase, the treated areas were assessed for visible changes according to the criteria of the Magnusson and Kligman scale, ISO 10993-10.

3. Intracutaneous Irritation Study

In this study, Sealant 4 prepared by Example 3 was adopted.

Intracutaneous irritation in response to the extracts of the sealant of the present disclosure was assessed in New Zealand White rabbits (BWs [gender]: >2 kg [male]; age: around 65 days, from the National Laboratory Animal Center, Taiwan). The testing was performed in compliance with ISO 10993-10. The rabbits were shaved to remove the fur at 5 sites and subsequently injected with an extract of a test compound at each site. The control solution (0.9% saline (polar control) and cottonseed oil [Sigma-Aldrich] (nonpolar control)) was injected into the same side of each rabbit, and dermal reactions were assessed at time points of 24, 48, and 72 hours.

4. Pyrogen Study in White Rabbits

In this study, Sealant 4 prepared by Example 3 was adopted.

The guidelines of USP39/NF34 (151) were followed to determine whether the test sample extracts passed the pyrogen evaluation in the New Zealand White rabbits (Hui Jun, BWs [gender]: >2 kg [male]; age: around 65 days) following a single dose injection (10 mL/kg) in an ear vein. 5 days before the experiment, the body temperatures of the rabbits were measured. The criteria for selecting rabbits for the pyrogen study were a body temperature that does not exceed 39.8° C. and no more than a 1° C. difference between the highest and lowest body temperatures among the 4 measurements. During the study, only reverse osmosis water was provided. The control temperature of each animal was determined using a rectal thermometer (accuracy ±0.1° C.). Every appliance used in the study was also pyrogen free. In the preliminary test, the control temperatures of the 3 animals were determined. Test samples (warmed up to 37±2° C.) were injected into an ear vein of an animal.

The administration time did not exceed 10 minutes. Body temperatures were measured 5 times at 30-minute intervals, at 1, 1.5, 2, 2.5, and 3 hours after administration. The elevations in body temperature of the animals were calculated by subtracting the control temperature from the highest of the 5 temperature measurements. The main test was performed with 5 additional animals when the results of the preliminary test indicated a fever (a high temperature).

5. Acute System Injection Study

In this study, Sealant 4 prepared by Example 3 was adopted.

A system toxicity study following the ISO 10993-11:2006 guidelines was performed to evaluate the toxicity response to extracts of the sealant of the present disclosure in mice (ICR mice, Bio-LASCO Taiwan Co., Ltd, Taipei, Taiwan; BWs [gender]: 17 to 23 g [male]). The test compound extracts were injected into mice at a dose of 50 mL test compound extract per kilogram BW. Control solutions of 0.9% saline for intravenous injections and cottonseed oil for intraperitoneal injections were given at a dose level of 50 mL/kg BW. Polar extracts were used for the intravenous injections, and nonpolar extracts were used for the intraperitoneal injections.

6. Wound Closure Animal Study

In this assay, Sealant 6 prepared by Example 3 was adopted.

To evaluate the bioadhesive property and the biocompatibility of the PEG-based hydrogels, rats (normal Sprague-Dawley [SD] rats, 100 to 150 g, 4 week old, male; Bio-LASCO Taiwan Co., Ltd) were anesthetized using Zoletil (Virbac, Taiwan, Taipei), and their backs were shaved. Skin incisions with 1.5 cm long and full-skin thickness deep were made on both sides of the backs of the rats. The skin incisions were quickly closed using Coloskin or the sealant of the present disclosure. The sealant of the present disclosure was sterilized by filtration using 200-nm syringe filters and prepared with a dual syringe kit. A 50-µL of aliquot of Coloskin or the sealant of the present disclosure was applied to the wound area. For the rats treated with the sealant of the present disclosure, after the sealant of the present disclosure was applied to the wound area, the wound area was irradiated with UV light for 60 seconds to cure the sealant. The wound regions were immediately photographed after wound closure and photographed on the $1^{st}$ and the $4^{th}$ day post-treatment. Moreover, the area of the wound regions were measured on the $7^{th}$ day post-treatment, and on the $14^{th}$ day post-treatment, the animals were sacrificed, the closed skin was harvested and fixed in paraformaldehyde (PFA) solution (3.7 wt. %) for histological analysis after hematoxylin and eosin (H&E) staining and Masson's trichrome stain (Sigma-Aldrich). The growth of collagen was calculated by using Image J software (National Institutes of Health (NIH), Bethesda, Md., USA).

7. Corneal Repair Study

In this study, Sealant 5 prepared by Example 3 was adopted.

The New Zealand white rabbits were divided into three groups, the suture stitching group, the Coloskin treatment group and the present disclosure sealant treatment group. On Day 0, a 3 mm long incision was made on the cornea of the eyes of white rabbits in each group, and treated with 9-0 suture, treated with Coloskin and treated with the present disclosure (after the present disclosure sealant was applied, it was irradiated with UV light (wavelength was 365 nm) for 10 seconds to cure the sealant) (suture stitching group: n=3;

Coloskin treatment group: n=3 and the present disclosure sealant treatment: n=4. n: number of eyes). On Day 3, the eyes of the white rabbits in each group were stained with fluorescent antibodies (Fluoro Touch (Fluorescein Sodium Ophthalmic Strips), Madhu Instruments Pvt. Ltd) to observe whether the wound had ulceration.

Thereafter, after the white rabbit was sacrificed, the eyeball tissue was removed and stored as a Davison fixative. Next, the cornea was sectioned and stained to observe the corneal state.

8. Statistical Analysis

All data are presented as the mean (standard deviation). The significance of differences between results was assessed via one-way analysis of variance (ANOVA) (EXCEL, Microsoft, Seattle, Wash., USA). For all tests, a P value <0.05 was considered statistically significant.

B. Results

1. In Vitro Cell Viability and MTT Assay

To evaluate the cytotoxicity of the sealant of the present disclosure, the effects of the samples on cell growth, morphology, and viability were evaluated. After cells were exposed to the extracts for 24 hours, the following items were evaluated:

Qualitative Determination

Figure 6:
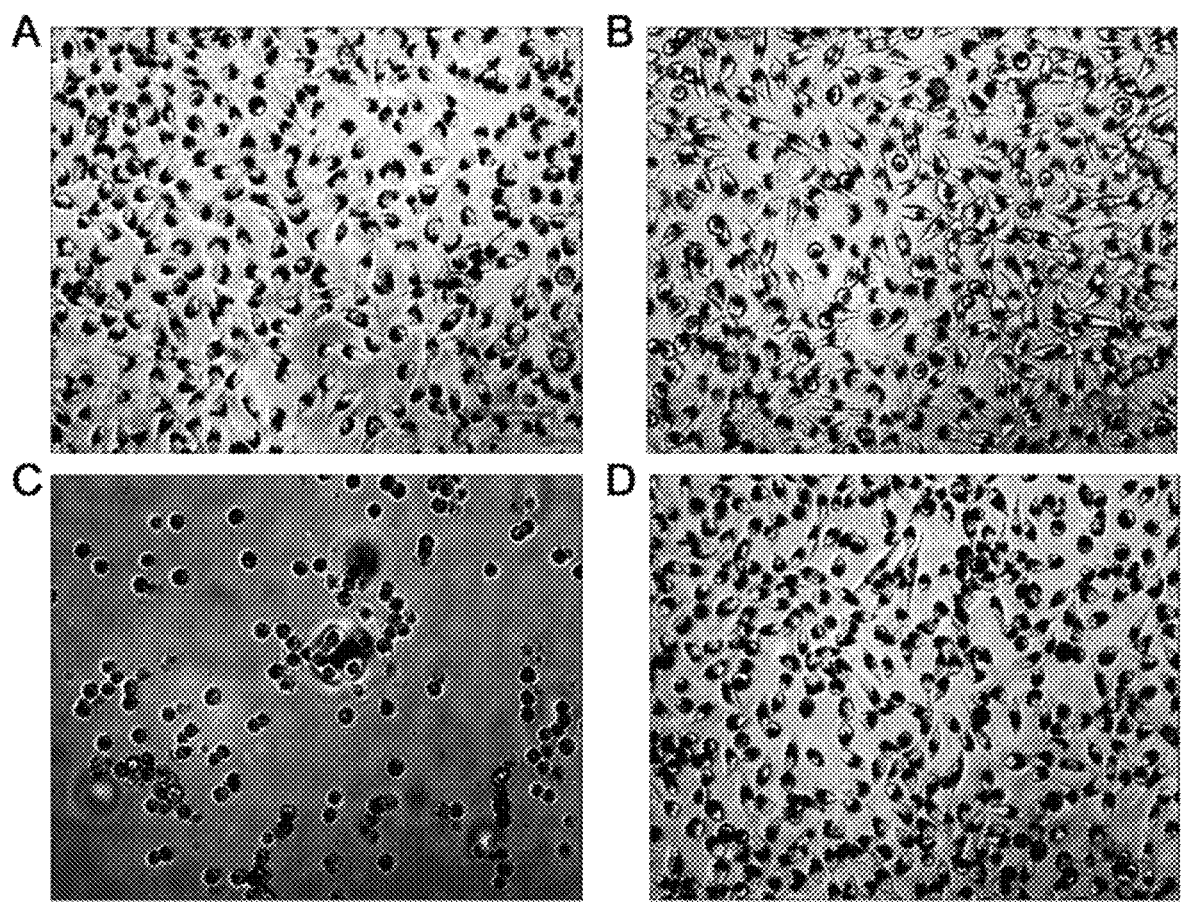
FIG. 6 shows the results of cytotoxicity analysis and 3-(4,5-Dimethyl-Thiazol-2-yl)-2,5-Diphenyltetrazolium (MTT) assay of the sealant of the present disclosure. After 24 hours of treatment, the cell morphology of L929 cells (mouse fibroblast cell line) was observed under a 100× inverted microscope. (A) Blank (B): culture solution; (B) Negative control (NC): high-density polyethylene; (C) Positive control (PC): 10% (v/v) dimethyl sulfoxide (DMSO); (D) Test sample (S): the sealant of the present disclosure.

A morphological assessment of L929 cells using an inverted microscope (100×) was performed after treating them with blank (B), negative control (NC), positive control (PC), or test sample (S) for 3 hours and staining them with neutral red. The morphology of blank (B)- and negative control (NC)-treated cells revealed a long spindle shape with obvious lamellipodia and filopodia instead of a lysed, rounded shape and inhibited growth. However, PC-treated cells showed a nearly complete rounded lysed morphology; cell layers were almost completely destroyed, and growth inhibition was observed. The cells treated with the test samples showed the same long spindle shape as cells treated with blank (B) and negative control (NC). According to the results of the microscopic assay, the percentages of rounded or lysed cells in the blank (B), negative control (NC), positive control (PC), and test sample (S) groups were 0%, 1%, 100%, and 5%, respectively. Therefore, the cytotoxicity of blank (B), negative control (NC), positive control (PC), and test sample (S) groups was graded at 0, 0, 4, and 0, respectively (Table 4 and FIG. 6).

Quantitative Determination

L929 cells were treated with blank (B), negative control (NC), positive control (PC), and test sample (S) for 24 hours, and cell viability was evaluated with an MTT cell proliferation/viability assay. The absorbance values of the blank (B), negative control (NC), positive control (PC), and test sample (S) groups at 570 nm were 1.065±0.071, 1.051±0.056, 0.294±0.038, and 0.861±0.053 respectively; the respective cell viability values were 100%, 99%, 28%, and 81%, and the respective mortality values were 0%, 1%, 72%, and 19% (Table 5).

TABLE 5

| Test Item | Absorbance (%) | Viability (%) | Mortality (%) |
| --- | --- | --- | --- |
| Blank (B) | 1.065 ± 0.071 | 100 | 0 |
| Negative control (NC) | 1.051 ± 0.056 | 99 | 1 |
| Positive control (PC) | 0.294 ± 0.038 | 28 | 72 |
| Test sample (S) | 0.861 ± 0.053 | 81 | 19 |

The qualitative and quantitative assay results (Table 4 and Table 5) indicated zero reactivity. Therefore, the extract solutions of the sealant of the present disclosure were considered to have no in vitro cytotoxicity.

2. Skin Sensitization Study

Figure 7A:
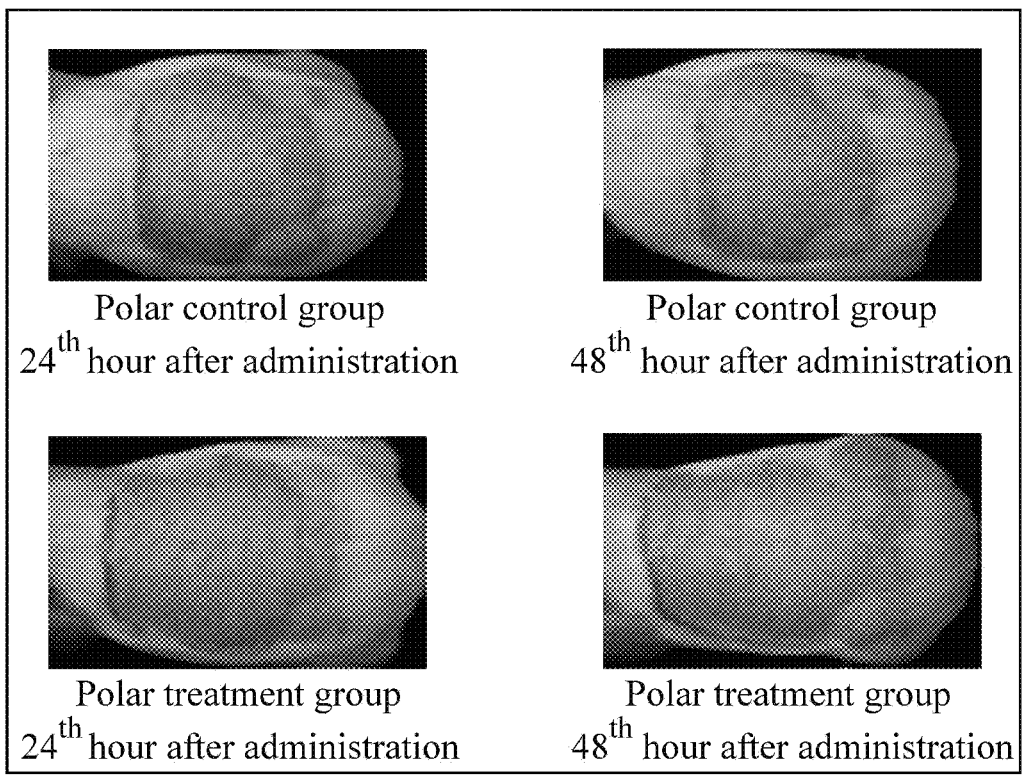
FIG. 7A shows a photograph of the observation of the skin reaction in the skin sensitization test for the sealant of the present disclosure (polar extract) (control group: 0.9% physiological saline)
Figure 7B:
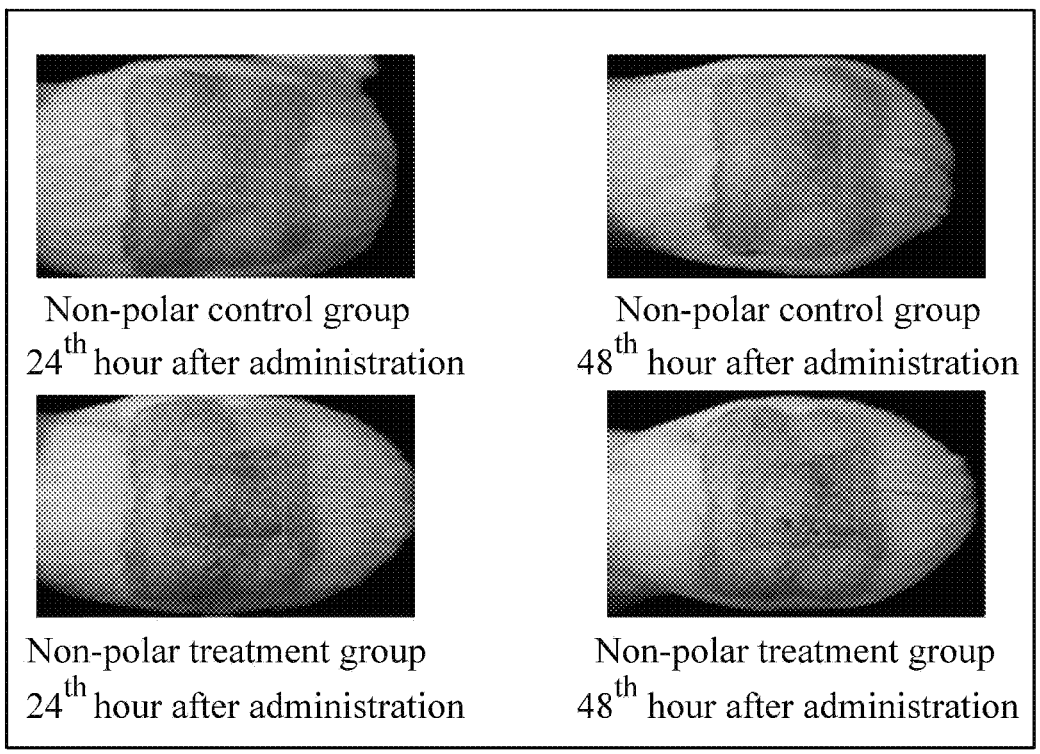
FIG. 7B shows a photograph of the observation of the skin reaction in the skin sensitization test for the sealant of the present disclosure (non-polar extract) (control group: cottonseed oil)
Figure 7C:
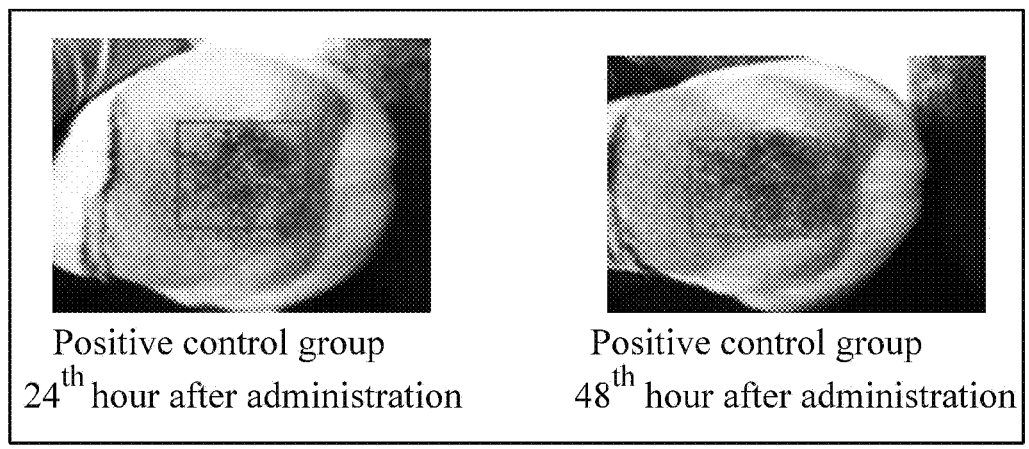
FIG. 7C shows a photograph of the observation of the skin reaction in the skin sensitization test for the sealant of the present disclosure (positive control: Coloskin)

The skin sensitization potential of the sealant of the present disclosure was tested on guinea pigs. Following extraction of the test samples, the extracts were applied twice in the induction phase and once in the challenge phase. Then, 24 hours and 48 hours after the challenge phase, neither the control nor the treatment group showed visible changes in the skin response on the treated areas (Table 5 and FIGS. 7A-C). The results indicated that the test samples (polar or nonpolar) did not cause delayed hypersensitivity on the skin of the tested guinea pigs.

TABLE 5

Skin reaction in guinea pigs.

| | Control | Treatment |
| --- | --- | --- |
| Group (0.9% saline) | | |
| Gender | Male | Male |
| Number of animals | 5 | 10 |
| Erythema and eschar | 0/5 | 0/10 |
| Edema | 0/5 | 0/10 |
| Group (cottonseed oil) | | |
| Gender | Male | Male |
| Number of animals | 5 | 10 |
| Erythema and eschar | 0/5 | 0/10 |
| Edema | 0/5 | 0/10 | n/n: Number of guinea pigs with abnormal clinical signs/number of guinea pigs per group.

3. Intracutaneous Irritation Study

Figure 8:
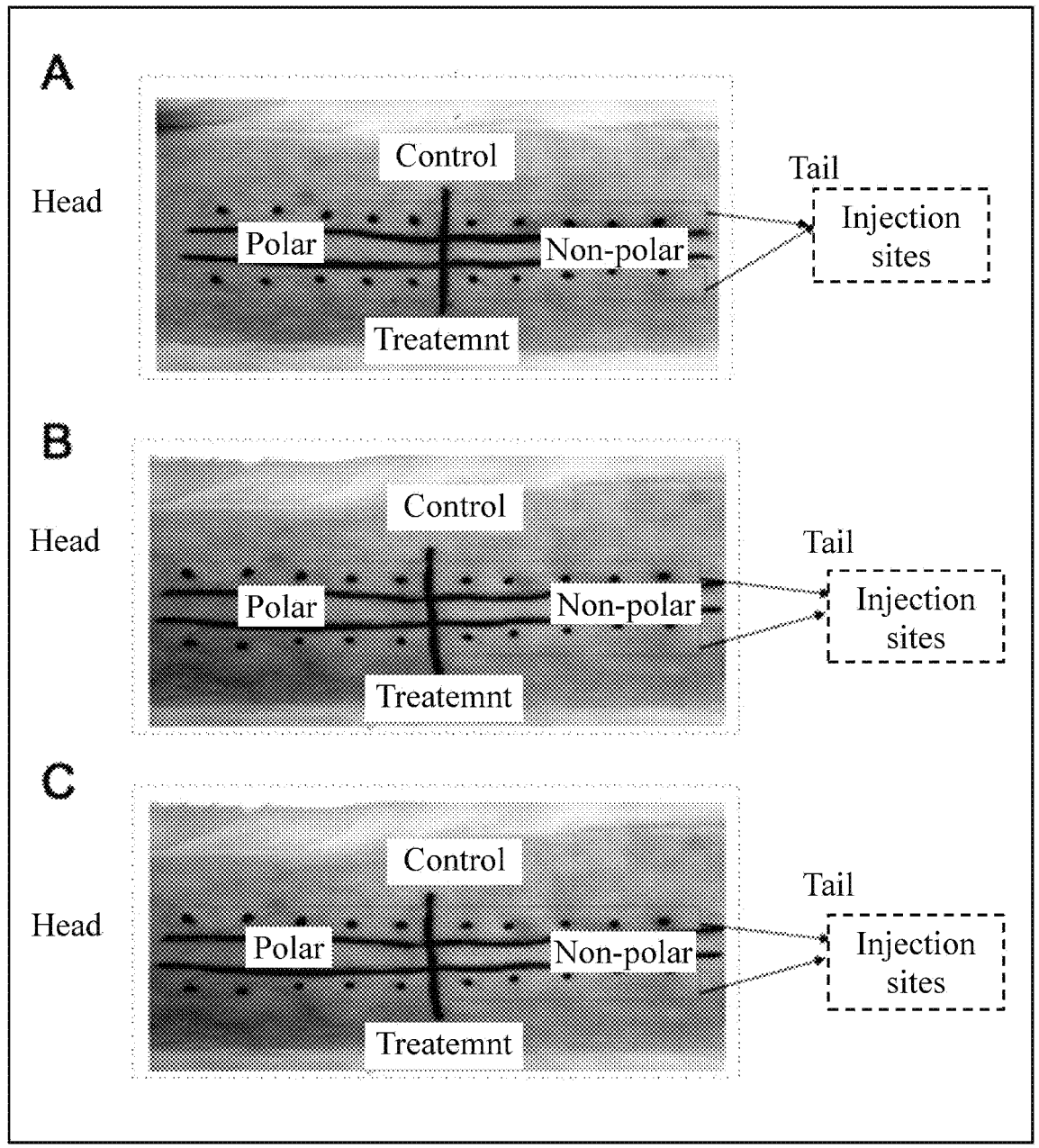
FIG. 8 shows the results of the intradermal stimulation study of the sealant of the present disclosure. (A) Observation at 24 hours after administration; (B) Observation at 48 hours after administration; (C) Observation at 72 hours after administration.

The intracutaneous irritation results showed that there were no significant clinical signs or gross findings in the control or treatment groups, and there was no mortality in any of the tested groups. Therefore, a single topical application of 0.2 mL of the test compound extracts did not cause intracutaneous irritation in New Zealand White rabbits. The intracutaneous irritation results showed that a single application of the test compound extracts induced neither observable clinical signs nor dermal gross changes in New Zealand White rabbits at any time point. Therefore, a single topical application of the sealant of the present disclosure did not cause observable irritation in New Zealand White rabbits (FIG. 8).

4. Pyrogen Study in White Rabbits

The BWs of 3 New Zealand White rabbits were above 1.5 kg, qualifying them for the study. The control temperatures of the 3 animals were 39.42° C., 39.37° C., and 39.25° C. Any elevation of body temperature for the 3 rabbits was below 0.5° C. (Table 6; Animal No. 79-1001: −0.46° C., Animal No. 79-1002: −0.10° C., and Animal No. 79-1003: −0.05° C.). The body temperature of the 3 qualifying White rabbits were measured 5 times after a single dose (10 mL/kg) of a compound was injected in an ear vein. The pyrogen response was negative for all samples; therefore, the samples were considered to have passed the pyrogen study.

TABLE 6

Pyrogen Study in White Rabbits.

(A) Control Temperature of Rabbits

| Animal number | Control temperature |
|---|---|
| 79-1001 | 39.42° C. |
| 79-1002 | 39.37° C. |
| 79-1003 | 39.25° C. |

(B) Temperature elevation

| Animal number | Elevation (body temperature after administration) |
|---|---|
| 79-1001 | −0.46° C. |
| 79-1002 | −0.10° C. |
| 79-1003 | −0.05° C. |

Temperature elevation: the highest body temperature (of the 5 measurements) minus the control temperature 5. Acute System Injection Study The toxicity response to the sealant of the present disclosure was assessed in mice after injecting the test samples and control solutions. The results showed that there were no significant clinical signs or gross findings in the control or treatment groups. Therefore, the test samples did not cause toxicity reactions or death after injection (Table 7). The study results showed that a single application of the hydrogels or the controls induced neither observable clinical signs nor gross findings in the mice at any time point. Therefore, the sealant of the present disclosure did not cause a toxicity reaction or death after injection (Table 7).

TABLE 7

Acute System Injection Study

(A) Incidence of Clinical Observation in Mice
Polar group

| Number of animals | 5 male | 5 male |
|---|---|---|
| Treated article | 0.9% saline | The sealant of the present disclosure |
| Toxicity reaction | 0/5 | 0/5 |
| Death | 0/5 | 0/5 |

Nonpolar group

| Number of animals | 5 male | 5 male |
|---|---|---|
| Treated article | Cottonseed oil | The sealant of the present disclosure |
| Toxicity reaction | 0/5 | 0/5 |
| Death | 0/5 | 0/5 |

(B) Incidence of Gross Finding
Polar group

TABLE 7-continued

Acute System Injection Study

| Dose level (mL/kg) | 50 | 50 |
|---|---|---|
| Gender | male | male |
| Animal number | 5 | 5 |
| Symptom | 0/5 | 0/5 |

Nonpolar group

| Dose level (mL/kg) | 50 | 50 |
|---|---|---|
| Gender | Male | Male |
| Animal number | 5 | 5 |
| Symptom | 0/5 | 0/5 | n/n: Number of mice with gross signs/number of mice per group

6. Wound Closure Animal Study

Figure 9A:
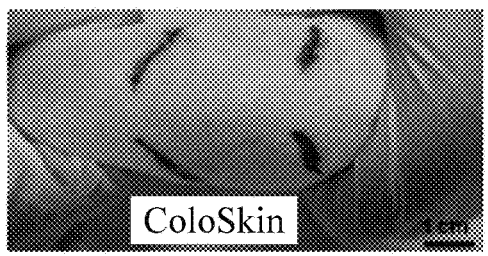
FIG. 9A shows photographs of the wound closure animal experiment. The skin incisions of the back of the rat were treated with Coloskin and the sealant of the present disclosure. (A) $1^{st}$ day after the treatment; (B) the $4^{th}$ day post-treatment; and (C) On the $14^{th}$ day post-treatment, closed skin was collected and fixed in a solution of formaldehyde (3.7% by weight) for use in histological analyses through hematoxylin and eosin (H&E) stain and Masson's trichrome stain.
Figure 9A:
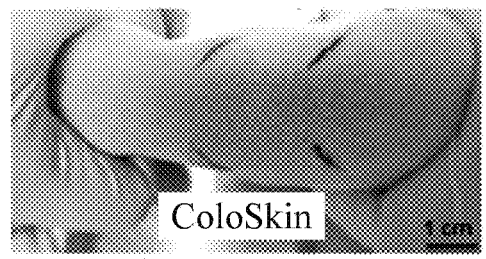
Figure 9A:
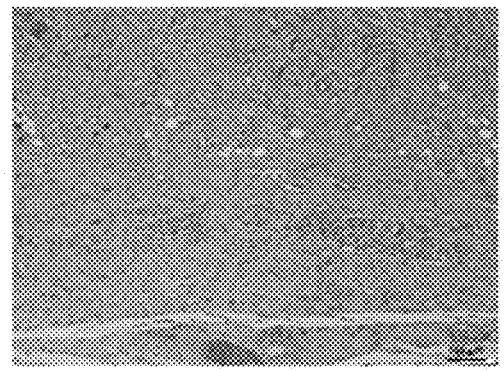
Figure 9A:
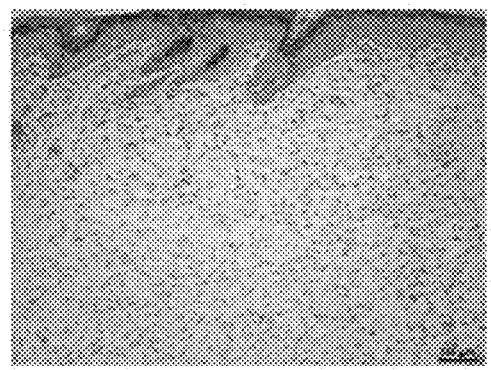
Figure 9A:
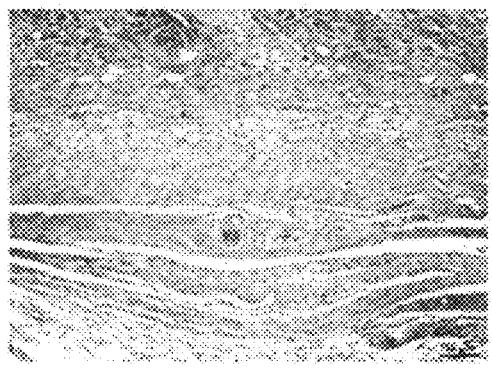
Figure 9A:
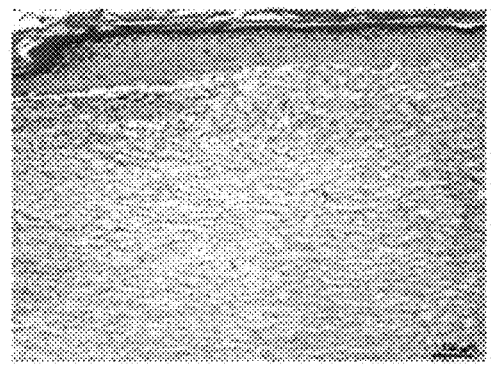
Figure 9B:
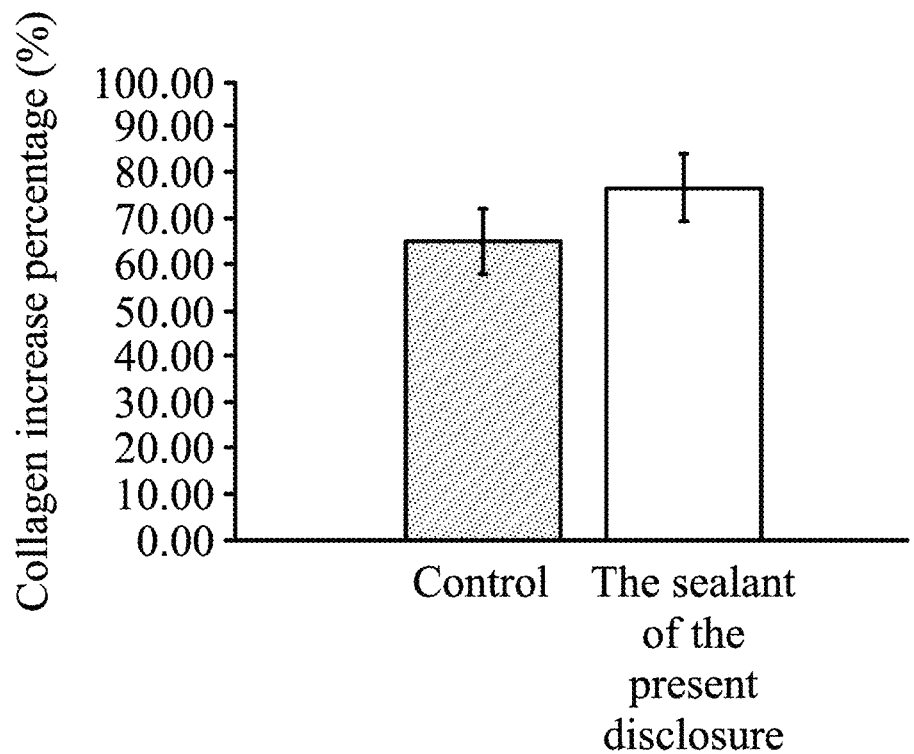
FIG. 9B shows the statistical results of collagen assays for the $14^{th}$ day post-treatment by Coloskin and the sealant of the present disclosure in the wound closure animal experiment (P<0.01)
Figure 9C:
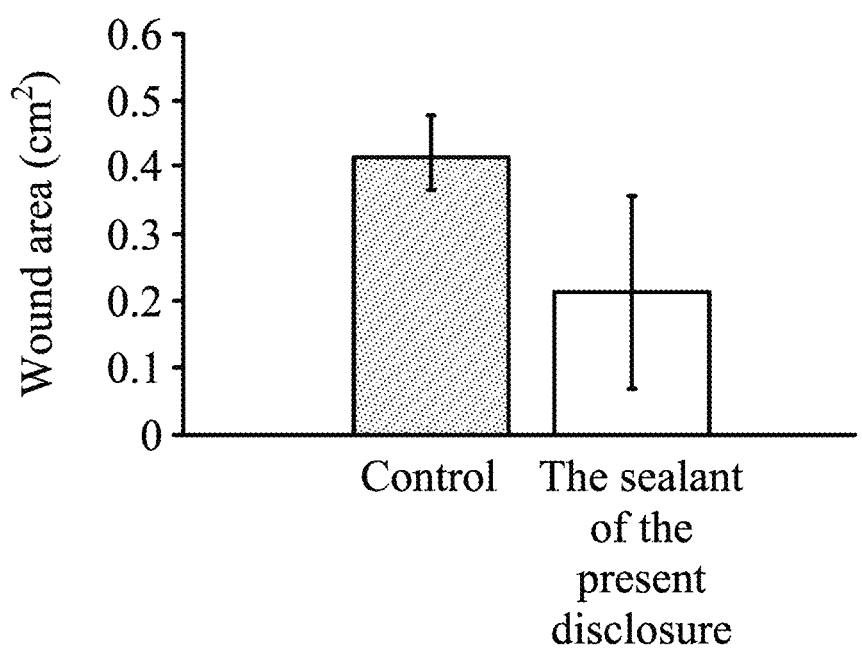
FIG. 9C shows the wound areas of various treatments on the $7^{th}$ day post-treatment by the sealant of the present disclosure in the wound closure animal experiment (P<0.01)

After applying the sealant of the present disclosure, bleeding from the incisions on the dorsum of SD rats immediately stopped, and the wound openings closed within minutes. The wound openings did not close after applying Coloskin. Furthermore, visual examinations were performed at different time points to compare the sealant of the present disclosure-treated incisions and Coloskin (a commercial product)-treated incisions. The results indicated that the sealant of the present disclosure enhanced the wound closure process (parts A and B part of FIG. 9A). The histological evaluation (H&E staining) showed that on the $14^{th}$ day post-treatment, there was more collagen at the wound sites in the group treated with the sealant of the present disclosure than in the Coloskin-treated group (part C of FIG. 9A). The average collagen in the Coloskin-treated group and the group treated with the sealant of the present disclosure were 65.2 and 77.2% (Image J), respectively (FIG. 9B). The wound area between 2 groups, and the average wound area in the Coloskin-treated group and the group treated with the sealant of the present disclosure were 0.4 $cm^2$ and 0.2 $cm^2$, respectively, after 7 days of treatment also calculated (FIG. 9C).

7. Corneal Repair Study

A 3 mm long incision was made on the cornea of the eyes of each group of white rabbits on Day 0 and sutured with a 9-0 suture, treated with Coloskin and treated with the present disclosure (after the present disclosure sealant was applied, it was irradiated with UV light (wavelength was 365 nm) for 10 seconds to cure the sealant. Thereafter, on Day 3, the eyes of each group of white rabbits were subjected to fluorescent antibody staining to observe whether the wound had ulceration.

Figure 10A:
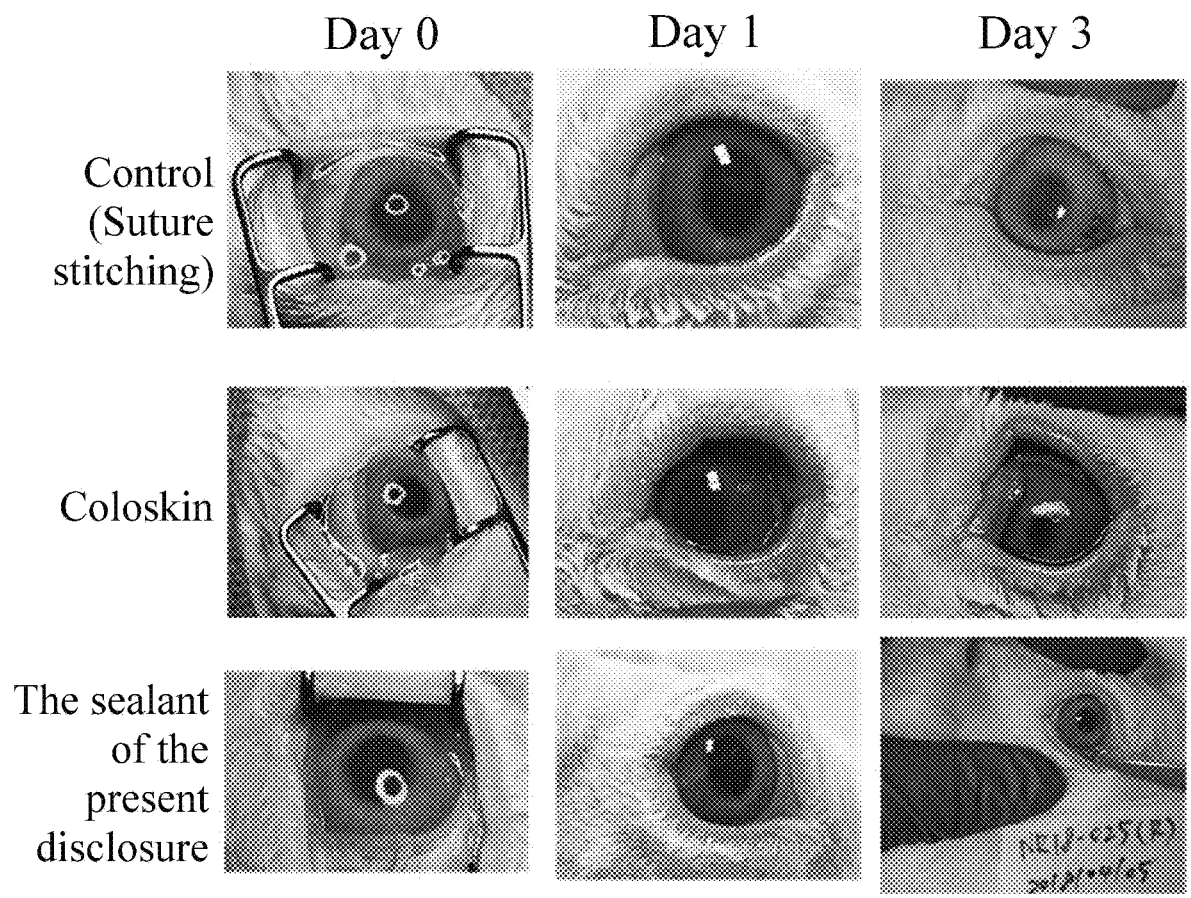
FIG. 10A shows photographs of Day 0, Day 1 and Day 3 after corneal incisions of the New Zealand White rabbit being sutured with 9-0 suture, treated with Coloskin and the sealant of the present disclosure.

The results are shown in FIG. 10A and Table 8.

TABLE 8

| Observation time after the surgery (Day) | The sealant of the present disclosure | | Coloskin | | 9-0 Surgical suture | |
|---|---|---|---|---|---|---|
| | Corneal fluorescence staining | Bacterial infection and inflammation | Corneal fluorescence staining | Bacterial infection and inflammation | Corneal fluorescence staining | Bacterial infection and inflammation |
| 3 | 0/6 | 0/6 | 1/4 | 0/4 | 0/4 | 0/4 | n/n: Number of eyes that are fluorescently stained (or eyes with inflammatory conditions)/number of eyes in each group Mann et al 2012 Toxicicogic Pathology FIG. 10A and Table 8 show that, except for the Coloskin treatment group in which it was found that the corneal wounds had ulceration and large-area staining, other groups of corneas were not stained by fluorescence. Therefore, in terms of corneal repair, the effect the sealant of the present disclosure is the same as that of a surgical suture. Also, no crystals or iris abnormalities were found in any of the groups.

Moreover, after the experiment was completed, the white rabbits were sacrificed, and corneal sections were obtained and observed, and the thickness of the wound area and of the non-wound area in the same cornea were measured. The observation results are shown in FIG. 10B.

Figure 10B:
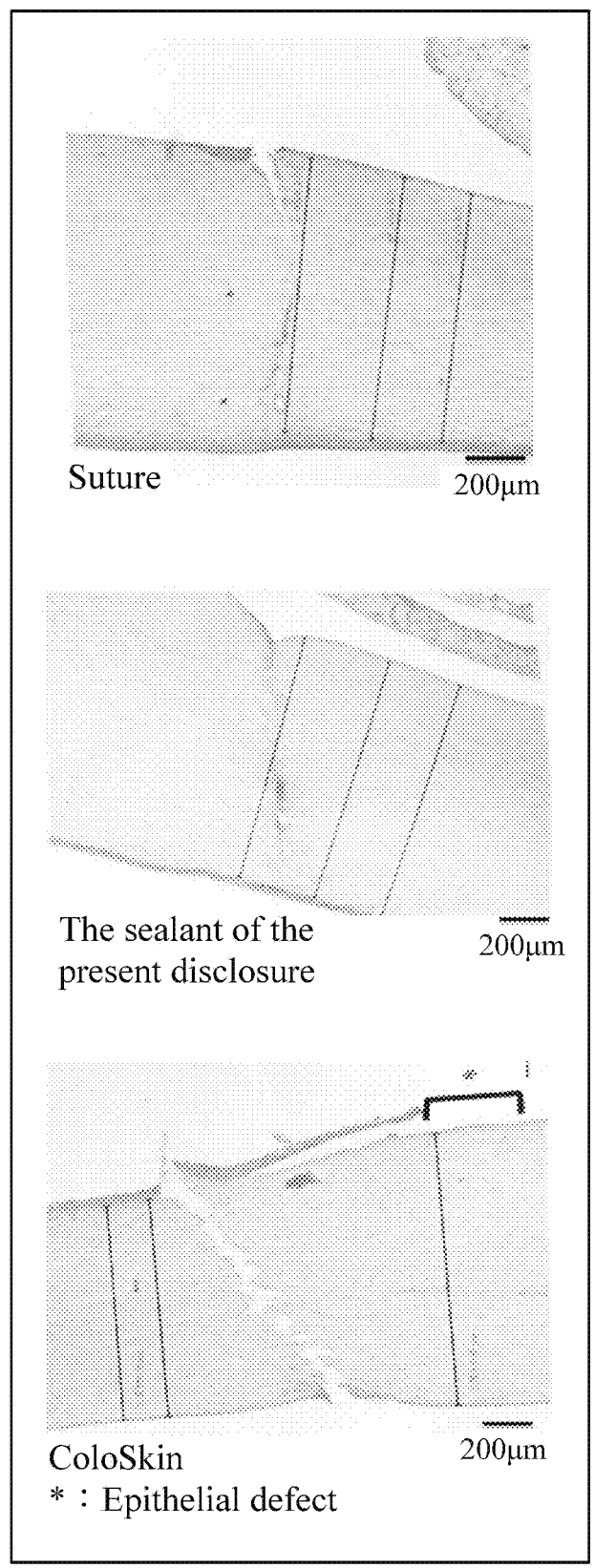
FIG. 10B shows the results of the corneas having been sliced and observed on Day 7 after the corneal incision of the New Zealand White rabbit was sutured with 9-0 suture, treated with Coloskin and the sealant of the present disclosure.

According to FIG. 10B, it is known that the corneas of the Coloskin-treated group had a defect while the group treated with the sealant of the present disclosure and the control group did not exhibit signs of this phenomenon.

Furthermore, corneas of the group treated with the sealant of the present disclosure and the control group were in the third or fourth phase of the corneal healing stage, whereas the corneas of Coloskin-treated group were in the first or second phase of the corneal healing stage.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A biodegradable sealant, consisting of:
   a polyethylene glycol derivative, wherein the polyethylene glycol derivative is obtained through a substitution reaction, and in the substitution reaction, polyethylene glycol is modified with methacrylic anhydride and the molecular weight of the polyethylene glycol used in the substitution reaction is 8000 or 35000;
   a photoinitiator; and
   a solvent,
   wherein the content of the polyethylene glycol derivative in the biodegradable sealant is 60-75 wt %.

2. The biodegradable sealant as claimed in claim 1, wherein the weight ratio of the polyethylene glycol used in the substitution reaction to the methacrylic anhydride used in the substitution reaction is 1:0.01-10.

3. The biodegradable sealant as claimed in claim 1, wherein the weight ratio of the polyethylene glycol used in the substitution reaction to the methacrylic anhydride used in the substitution reaction is 1:1-10.

4. The biodegradable sealant as claimed in claim 1, wherein the molecular weight of the polyethylene glycol used in the substitution reaction is 8000, and the weight ratio of the polyethylene glycol used in the substitution reaction to the methacrylic anhydride used in the substitution reaction is 1:0.05-1.5.

5. The biodegradable sealant as claimed in claim 1, wherein the molecular weight of the polyethylene glycol used in the substitution reaction is 35000, and the weight ratio of the polyethylene glycol used in the substitution reaction to the methacrylic anhydride used in the substitution reaction is 1:0.05-0.8.

6. The biodegradable sealant as claimed in claim 1, wherein in the polyethylene glycol derivative, the degree of substitution of the methacrylic anhydride is 60-100%.

7. The biodegradable sealant as claimed in claim 1, wherein the weight ratio of the polyethylene glycol derivative to the photoinitiator is 1:0.001-0.01.

8. The biodegradable sealant as claimed in claim 1, wherein the photoinitiator comprises a UV photoinitiator.

9. The biodegradable sealant as claimed in claim 8, wherein the UV photoinitiator comprises riboflavin, 2-hydroxy-4'-(2-hydroxyethoxy)-2-methylpropiophenone or phenylbis(2,4,6-trimethylbenzoyl)phosphine oxide.

10. The biodegradable sealant as claimed in claim 1, wherein the solvent comprises water.

11. The biodegradable sealant as claimed in claim 1, wherein the osmotic pressure of the biodegradable sealant is 300-450 mOsm/kg.

12. The biodegradable sealant as claimed in claim 1, wherein the in vitro degradation time for the biodegradable sealant is 70-90 hours and the in vitro condition is in distilled water.

13. The biodegradable sealant as claimed in claim 1, wherein the pH value of the biodegradable sealant is 6.0-7.5.

14. A method for bonding or repairing of biological tissue, comprising:
    applying the biodegradable sealant as claimed in claim 1 to a biological tissue to be bonded or repaired.

15. The method for bonding or repairing of biological tissue as claimed in claim 14, further comprising:
    after applying the biodegradable sealant to the biological tissue to be bonded or repaired, performing an illumination procedure on the biological tissue to be bonded or repaired to make the agent for bond or repair of biological tissue solidify to bond or repair the biological tissue to be bonded or repaired.

16. The method for bonding or repairing of biological tissue as claimed in claim 14, wherein the weight ratio of the polyethylene glycol used in the substitution reaction to the methacrylic anhydride used in the substitution reaction is 1:0.01-10.

17. The method for bonding or repairing of biological tissue as claimed in claim 14, wherein in the polyethylene glycol derivative, the degree of substitution of the methacrylic anhydride is 60-100%.

18. The method for bonding or repairing of biological tissue as claimed in claim 14, wherein the weight ratio of the polyethylene glycol derivative to the photoinitiator is 1:0.001-0.01.

19. The method for bonding or repairing of biological tissue as claimed in claim 15, wherein the time it takes to perform the illumination procedure is 10-60 seconds.

20. The method for bonding or repairing of biological tissue as claimed in claim 15, wherein the illumination procedure is performed by UV light, and the wavelength of the UV light is 200-450 nm.

21. The method for bonding or repairing of biological tissue as claimed in claim 15, wherein the photoinitiator is a UV photoinitiator, and the UV photoinitiator comprises riboflavin, 2-hydroxy-4'-(2-hydroxyethoxy)-2-methylpropiophenone or phenylbis(2,4,6-trimethylbenzoyl)phosphine oxide.

22. The method for bonding or repairing of biological tissue as claimed in claim 15, wherein the biological tissue to be bonded or repaired is a wound in a subject.

23. The method for bonding or repairing of biological tissue as claimed in claim 22, wherein the wound is a skin wound or an eye wound.

24. The method for bonding or repairing of biological tissue as claimed in claim 22, wherein the wound is a skin wound, and wherein the molecular weight of the polyethylene glycol used in the substitution reaction is 35000.

25. The method for bonding or repairing of biological tissue as claimed in claim 22, wherein the wound is an eye wound, and wherein the molecular weight of the polyethylene glycol used in the substitution reaction is 8000.

* * * * *